United States Patent
Jacob

(10) Patent No.: US 12,055,539 B2
(45) Date of Patent: Aug. 6, 2024

(54) HDAC1/2 ACTIVATOR FOR PROMOTING AND/OR ACCELERATING MYELINATION AND/OR REMYELINATION

(71) Applicant: UNIVERSITE DE FRIBOURG, Fribourg (CH)

(72) Inventor: Claire Jacob, Basel (CH)

(73) Assignee: UNIVERSITE DE FRIBOURG, Fribourg (CH)

( * ) Notice: Subject to any disclaimer, the term of this patent is extended or adjusted under 35 U.S.C. 154(b) by 0 days.

(21) Appl. No.: 16/617,027

(22) PCT Filed: Jun. 8, 2018

(86) PCT No.: PCT/EP2018/065168
§ 371 (c)(1),
(2) Date: Nov. 26, 2019

(87) PCT Pub. No.: WO2018/224650
PCT Pub. Date: Dec. 13, 2018

(65) Prior Publication Data
US 2020/0182859 A1    Jun. 11, 2020

(30) Foreign Application Priority Data

Jun. 8, 2017    (EP) .................................. 17174916

(51) Int. Cl.
G01N 33/50    (2006.01)
A61K 31/522    (2006.01)
A61K 45/06    (2006.01)
A61P 25/28    (2006.01)

(52) U.S. Cl.
CPC ....... *G01N 33/5023* (2013.01); *A61K 31/522* (2013.01); *A61K 45/06* (2013.01); *A61P 25/28* (2018.01); *G01N 2333/98* (2013.01); *G01N 2500/10* (2013.01)

(58) Field of Classification Search
CPC ........... G01N 33/5023; G01N 2333/98; G01N 2500/10; G01N 2500/20; G01N 33/573; A61P 25/28; A61K 31/522; A61K 45/06; A61K 31/52
See application file for complete search history.

(56) References Cited

U.S. PATENT DOCUMENTS

| | | | |
|---|---|---|---|
| 6,277,402 B1 * | 8/2001 | DeLack | A61K 31/417 424/443 |
| 2007/0134210 A1 | 6/2007 | Heidaran | |
| 2015/0272936 A1 * | 10/2015 | Vakkalanka | A61P 9/00 514/263.21 |
| 2016/0166687 A1 | 6/2016 | Schultz et al. | |
| 2017/0157127 A1 * | 6/2017 | Longo | A61P 25/00 |

FOREIGN PATENT DOCUMENTS

| | | |
|---|---|---|
| EP | 2581088 A1 | 4/2013 |
| WO | 00/00184 A2 | 1/2000 |
| WO | 01/67107 A1 | 9/2001 |
| WO | 03/094957 A2 | 11/2003 |
| WO | 2008/011083 A2 | 1/2008 |
| WO | 2010/011318 A2 | 1/2010 |

OTHER PUBLICATIONS

Multiple Sclerosis Society study—Study will look at the impact of chocolate on MS; retrieved from the web on Mar. 7, 2021 (Year: 2015).*
Wikipedia entry for theophylline; retrieved from the web on Mar. 8, 2021 (Year: 2021).*
Shelly Coe et al., A randomised double-blind placebo-controlled feasibility trial of flavonoid-rich cocoa for fatigue in people with relapsing and remitting multiple sclerosis, J Neurol Neurosurg Psychiatry 2019;90:507-513. doi:10.1136/jnnp-2018-319496 (Year: 2019).*
Lassmann H., (2019) Pathogenic Mechanisms Associated With Different Clinical Courses of Multiple Sclerosis. Front. Immunol. 9: 3116. doi: 10.3389/fimmu.2018.03116) (Year: 2019).*
Janitschke et al., Methylxanthines and Neurodegenerative Diseases: An Update, Nutrients 2021, 13, 803.*
Mastbergen et al., The mechanism of action of doxofylline is unrelated to HDAC inhibition, PDE inhibition or adenosine receptor antagonism, Pulmonary Pharmacology & Therapeutics, 25 (2012) 55e61.*
Yoneda et al., Theobromine up-regulates cerebral brain-derived neurotrophic factor and facilitates motor learning in mice, Journal of Nutritional Biochemistry 39 (2017) 110-116.*
Weng, Q., et al., "5-Fluorouracil causes severe CNS demyelination by disruption of TCF7L2/HDAC1/HDAC2 complex in adolescent mice" Toxicology (2014) 325:144-50.
Chen, Y., et al., "HDAC-mediated deacetylation of NF-κB is critical for Schwann cell myelination" Nat. Neurosci. (2011) 14(4):437-41.
Ye, F., et al., "HDAC1 and HDAC2 regulate oligodendrocyte differentiation by disrupting the beta-catenin-TCF Interaction" Nat. Neurosci. (2009) 12(7):829-38.

(Continued)

*Primary Examiner* — Svetlana M Ivanova

(74) *Attorney, Agent, or Firm* — Robert C. Netter, Jr.; Dann, Dorfman, Herrell & Skillman

(57) ABSTRACT

The present invention is based on the surprising finding of the property of promoting myelination of activators of histone deacetylase (HDAC) 1 and 2. In particular, such activators have the capacity of accelerating and increasing remyelination after lesions to the myelin of nerve cells of the peripheral and central nervous systems. The present inventor found that HDAC2 deacetylates eEF1A1 and thereby prevents the latter from removing outside the nucleus key inducers of myelin genes transcription. The HDAC1/2 activators are useful in the treatment of diseases associated with demyelination, such as Multiple Sclerosis.

17 Claims, 12 Drawing Sheets

(56) References Cited

OTHER PUBLICATIONS

Jacob, C., et al., "HDAC1 and HDAC2 control the transcriptional program of myelination and the survival of Schwann cells" Nat. Neurosci. (2011) 14(4):429-36.
Wu, M., et al.,, "Differential modulation of the oligodendrocyte transcriptome by sonic hedgehog and bone morphogenetic protein 4 via opposing effects on histone acetylation" J. Neurosci. (2012) 32(19):6651-64.
Wheeler, N., et al., "The Autotaxin-Lysophosphatidic Acid Axis Modulates Histone Acetylation and Gene Expression during Oligodendrocyte Differentiation" J. Neurosci. (2015) 35(32):11399-414.
Jacob, C., et al., "How histone deacetylases control myelination" Mol. Neurobiol. (2011) 44(3):303-12.
Bondan, E., et al., "Effects of propentofylline on CNS remyelination in the rat brainstem" Microsc. Res. Tech. (2014) 77(1):23-30.
Qu, X., et al., "Quercetin improves hypoxia-ischemia induced cognitive deficits via promoting remyelination in neonatal rat" Brain Res. (2014) 1553:31-40.
Yang, H., et al., "G protein-coupled receptor 37 is a negative regulator of oligodendrocyte differentiation and myelination" Nat. Commun. (2016) 7:10884.
Deshmukh, V., et al., "A regenerative approach to the treatment of multiple sclerosis" Nature (2013) 502(7471):327-332.
Iseri, et al., "The effect of pulse methylprednisolone plus theophylline treatment on clinical, pulmonary and Inflammatory markers in relapses of multiple sclerosis" Balkan Med. J. (2013) 30(1):33-6.
Yan, et al., "Flavonoids potentiated anticancer activity of cisplatin in non-small cell lung cancer cells in vitro by inhibiting histone deacetylases" Life Sciences (2020) 258:118211.
Jean-Marie, et al., "Benefits of Polyphenols and Methylxanthines from Cocoa Beans on Dietary Metabolic Disorders" Foods (2021) 10:2049.
Chen, et al., "Effects of caffeine on cell viability and activity of histone deacetylase 1 and histone acetyltransferase in glioma cells" Tzu Chi Medical Journal (2016) 28:103e108.
National Multiple Sclerosis Society, "Disease-Modifying Therapies for MS" (2022) available at https://www.nationalmssociety.org/Programs-and-Services/Resources/The-MS-Disease-Modifying-Medications-(-pdf).
Jiang, et al., "Histamine H2 receptor negatively regulates oligodendrocyte differentiation in neonatal hypoxic-ischemic white matter injury" J. Exp. Med. (2020) 218(1):e20191365.
Green, et al., "Clemastine fumarate as a remyelinating therapy for multiple sclerosis (ReBuild): a randomised, controlled, double-blind, crossover trial" Lancet (2017) 390:2481-89.
Journey, et al., "Theophylline Toxicity" (2022) NCBI Bookshelf, StatPearls Publishing (FL), available at https://www.ncbi.nlm.nih.gov/books/NBK532962/?report=printable.
Rabe, et al., "Theophylline and selective PDE inhibitors as bronchodilators and smooth muscle relaxants" Eur. Respir. J. (1995) 8:637-642.
Barnes, P.J., "Theophylline" Pharmaceuticals (2010) 3:725-747.
Colussi, et al., "HDAC2 blockade by nitric oxide and histone deacetylase inhibitors reveals a common target in Duchenne muscular dystrophy treatment" PNAS (2008) 105(49):19183-19187.
Ito, et al., "A molecular mechanism of action of theophylline: Induction of histone deacetylase activity to decrease inflammatory gene expression" PNAS (2002) 99(13):8921-8926.
Thermo Scientific Chemicals, "Histamine diphosphate, 98%", available at https://www.fishersci.de/shop/products/histamine-diphosphate-98-therm.
IARC Monographs on the Evaluation of Carcinogenic Risks to Humans, vol. 51 (1991) Lyon (FR), International Agency for Research on Cancer, Caffeine chapter, available at www.ncbi.nlm.nih.gov/books/NBK507027/.
IARC Monographs on the Evaluation of Carcinogenic Risks to Humans, vol. 51 (1991) Lyon (FR), International Agency for Research on Cancer, Theophylline chapter, available at www.ncbi.nlm.nih.gov/books/NBK507021/.
Nehling, et al., "Caffeine and the central nervous system: mechanisms of action, biochemical, metyabolic and [pyschostimulant effects" Brain Res. Rev. (1992) 17:139-170.
Fiani, et al., "The neurophysiology of caffeine as a central nervous system stimulant and the resultant effects on cognitive function" Cureus (13(5):e15032.
McLellan, et al., "A review of caffeine's effect on cognitive, physical and occupational performance" Neurosci. Biobehav. Rev. (2016) 71:294-312.

\* cited by examiner

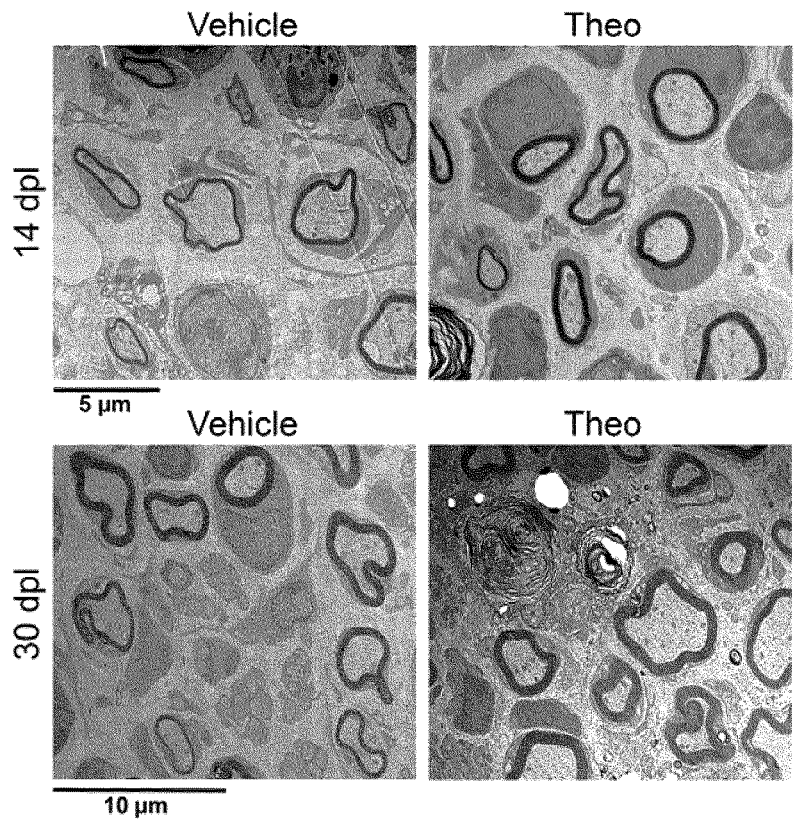
Figure 5
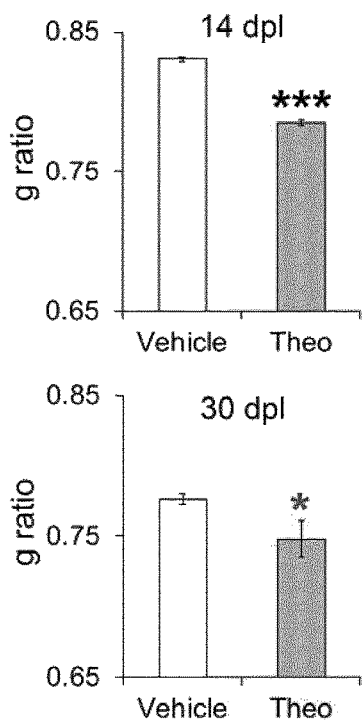
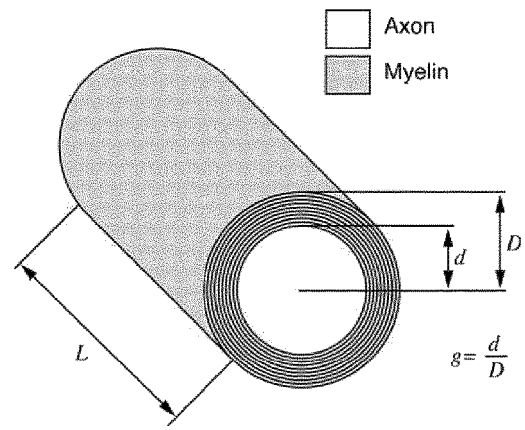
Figure 6B
Figure 6A

HDAC1/2 ACTIVATOR FOR PROMOTING AND/OR ACCELERATING MYELINATION AND/OR REMYELINATION

The present application is § 371 application of PCT/EP2018/065168, filed Jun. 8, 2018, which claims priority to EP Application No. 17174916.1, filed Jun. 8, 2017. The entire disclosure of each of the foregoing applications is incorporated by reference herein.

TECHNICAL FIELD

The present invention relates to an histone deacetylase 1 and/or 2 (HDSC1/2) activator for promoting myelination, for accelerating remyelination after lesions to nerve cells, for treating diseases associated with demyelination, to methods for screening agents useful in the treatment of such diseases, and to methods of treatment.

BACKGROUND ART AND PROBLEMS SOLVED BY THE INVENTION

Multiple Sclerosis (MS) is a demyelinating disease in which the insulating sheaths of nerve cells in the brain, optic nerves and/or spinal cord are damaged. This damage disrupts the ability of parts of the nervous system to communicate, resulting in a range of signs and symptoms, including physical and mental problems. MS is the most frequent degenerative disease of the central nervous system (CNS), the onset of which is often between 20 and 50 years old. While there are treatments allowing alleviating the symptoms of the disease, there is presently no cure for MS. There are several factors reported to trigger the onset, such as viral infection, food, genetics and environmental factors.

On the cellular level, MS starts with attacks affecting oligodendrocytes, the cells that produce the myelin sheaths of axons in the CNS. These attacks are caused, at least in part, by a person's own immune system, which is why MS is believed to be an immune-mediated disorder. Following an attack of the myelin sheaths, new oligodendrocytes are generally recruited to the site of lesion, where they regenerate the myelin sheath in a process referred to as remyelination. Recurrent attacks and regeneration result in the pattern of successive relapsing and remitting phases typical for early stages. MS evolves later into a progressive neurodegenerative disease where neurons are lost. Indeed, in this later stage, remyelination does no longer occur or is not effective, resulting in neuronal loss.

MS is one of a series of demyelination disorders. The latter can affect the CNS as well as the peripheral nervous system (PNS). For example, demyelination occurs after traumatic lesions of the CNS and the PNS.

The myelin sheath, which serves to increase nerve conduction velocities, is deposited around axons by specialized cells in the central and peripheral nervous systems of higher vertebrates. Indeed, myelin is synthesized by oligodendrocytes in the CNS (as already mentioned above) and by Schwann cells in the PNS.

Brügger et al, 2016 (ref. 1) have reported that, after sciatic nerve crush lesion, HDAC2 coordinates the action of other chromatin-remodelling enzymes to induce the upregulation of Oct6, a key transcription factor for the development of Schwann cells. After injury, mature Schwann cells convert into repair cells that foster axonal regrowth, and redifferentiate to rebuild myelin. The authors report that short-term HDAC1/2 inhibitor treatment early after lesion acceleration functional recovery and enhances regeneration of the crushed nerve cells of the PNS.

More specifically, Brügger et al, 2016 (ref. 1) have shown that HDAC2 interacts with the transcription factor Sox10 and recruits histone H3 lysine 9 (H3K9) demethylases (HDMs) to form a multifunctional protein complex that de-represses the Sox10 target genes Oct6 and Krox20 to allow their subsequent activation at different time points of the regeneration process after lesion. Inactivating this mechanism was shown to result in earlier conversion into repair Schwann cells after lesion and faster axonal regeneration.

It is an objective underlying the present invention to further elucidate the role of HDAC2 in the regeneration process after lesion. It is an objective of the present invention to elucidate the mechanisms controlling Schwann cell conversion into repair cells and dedifferentiation after lesion.

It is a further objective underlying the present invention to provide novel therapeutic strategies for the treatment of diseases and neural damages associated with demyelination in both, the PNS and the CNS. In particular, it is an objective of the invention to provide a treatment of MS and other demyelinating diseases. It is also an objective of the invention to provide compounds capable of promoting, accelerating and/or increasing remyelination. It is an objective to provide novel assays for screening compounds suitable to prevent or treat demyelination and for promoting remyelination.

U.S. Pat. No. 6,277,402 discloses a method for treating multiple sclerosis, the method comprising administering a histamine H2 agonist and a phosphodiesterase inhibitor. The present invention is not concerned with histamine H2 agonists and phosphodiesterase inhibitors.

US2003/0134865 discloses a method for screening comprising the step of exposing a xanthine compound to a histone deacetylase. According to this reference, screened compounds are useful in treating conditions caused by or exhibiting abnormal cellular proliferation or differentiation, such as cancer, or inflammation, in particular asthma or other inflammatory airway disease, such as COPD (Chronic obstructive pulmonary disease). The present invention is not concerned with these conditions.

Treatments of MS that are currently available are basically based in anti-inflammatory agents. These agents are capable of counteracting damages to nerve cells caused by the patient's immune cells and thereby prevent attacks against nerve cells characteristic of MS or reduce the frequency of such attacks. After such an attack, the nerve cells are capable of regenerating to some extent, but the capacity of regeneration diminishes with the progression of the disease and also with age. In particular, said currently available treatments do not act directly on the regeneration of the damaged tissue.

SUMMARY OF THE INVENTION

The present invention provides compounds, methods, treatments and/or combinatory treatments for addressing the problems depicted herein above.

Remarkably, the present inventor provides evidence for the biological activity of activators of HDAC1/2, in particular HDAC2, with respect to the myelination and remyelination of nerve cells in both, the PNS and the CNS.

In an aspect, the invention provides an activator of HDAC (histone deacetylase) 1 or 2 (increasing HDAC1/2 activity and/or expression) for increasing, accelerating and/or promoting myelination.

In an aspect, the invention provides an activator of HDAC (histone deacetylase) 1 or 2 (increasing HDAC1/2 activity and/or expression) for increasing, accelerating and/or promoting remyelination.

In an aspect, the invention provides an activator of HDAC (histone deacetylase) 1 or 2 (increasing HDAC1/2 activity and/or expression) for increasing, accelerating and/or promoting remyelination after lesions to myelin of nerve cells.

In an aspect, the invention provides an activator of HDAC (histone deacetylase) 1 or 2 (increasing HDAC1/2 activity and/or expression) for treating and/or preventing a demyelinating disease.

In an aspect, the invention provides an activator of HDAC (histone deacetylase) 1 or 2 (increasing HDAC1/2 activity and/or expression), such as theophylline, for treating and/or preventing multiple sclerosis.

In an aspect, the invention provides an activator of HDAC (histone deacetylase) 1 or 2 (increasing HDAC1/2 activity and/or expression) for treating and/or preventing one or more conditions selected from the group consisting of: (1) traumatic injury of the PNS, (2) multiple sclerosis, (3) Charcot-Marie-Tooth disease, (4) Waardenburg syndrome, (5) Guillain-Barré syndrome, (6) chronic inflammatory demyelination polyneuropathy, (7) demyelination due to aging, diabetes or due to toxic agents, (8) demyelination and hypomyelination due to other diseases, such as Acute disseminated encephalomyelitis, transverse myelitis, Leukodystrophy, Central pontine myelinolysis, Glioma, (9) schizophrenia, (10) demyelination after traumatic lesion of the CNS.

In an aspect, the invention provides a method for screening for agents suitable in the treatment and/or prevention of a disease or condition associated with demyelination, and/or for screening for agents suitable for promoting myelination and/or for increasing and/or accelerating remyelination, the method comprising:
 assessing the capacity of a candidate agent to increase the HDAC1/2 activity and/or expression,
 wherein presence of capacity to increase HDAC1/2 activity and/or expression indicates that said candidate agent is an agent suitable for the treatment of said diseases and for promoting myelination.

In an aspect, the invention provides a method for treating and/or preventing a disease or condition associated with demyelination, the method comprising the step of administering, to a subject in need thereof, an activator of HDAC1 and/or HDAC2.

In an aspect, the invention provides a method for increasing, accelerating and/or promoting the remyelination of nerve cells, the method comprising the step of administering, to a subject in need thereof, an activator of HDAC1 and/or HDAC2.

In an aspect, the invention provides an activator of HDAC (histone deacetylase) 1 or 2 enzymatic activity and/or expression, such as theophylline, in combination with an anti-inflammatory agent, for treating and/or preventing one or more conditions specified herein above, in particular multiple sclerosis.

In an aspect, the invention provides a method for treating and/or preventing one or more conditions specified herein above, in particular multiple sclerosis, the method comprising administering an activator of HDAC (histone deacetylase) 1 or 2 enzymatic activity and/or expression, for example theophylline, in combination with an anti-inflammatory agent.

Further aspects and preferred embodiments of the invention are defined herein below and in the appended claims. Further features and advantages of the invention will become apparent to the skilled person from the description of the preferred embodiments given below.

BRIEF DESCRIPTION OF THE DRAWINGS

FIG. 5 shows electron microscopy images of cross-sections of injured sciatic nerves at 14 and 30 dpl, following administration of the HDAC2 activator theophylline or its vehicle. When the activator was administered, the myelin sheaths (black rings) appeared thicker compared to images obtained from control samples.

FIG. 6A shows the g-ratio determined from samples as described with respect to FIGS. 4A and 4B, at 14 and 30 dpl, respectively. When the HDAC2 activator was administered, the g-ratio was significantly lower, demonstrating increased myelin thickness. FIG. 6B illustrates the parameters used for determining the g-ratio mentioned with respect to FIG. 6A.

Figure 1:
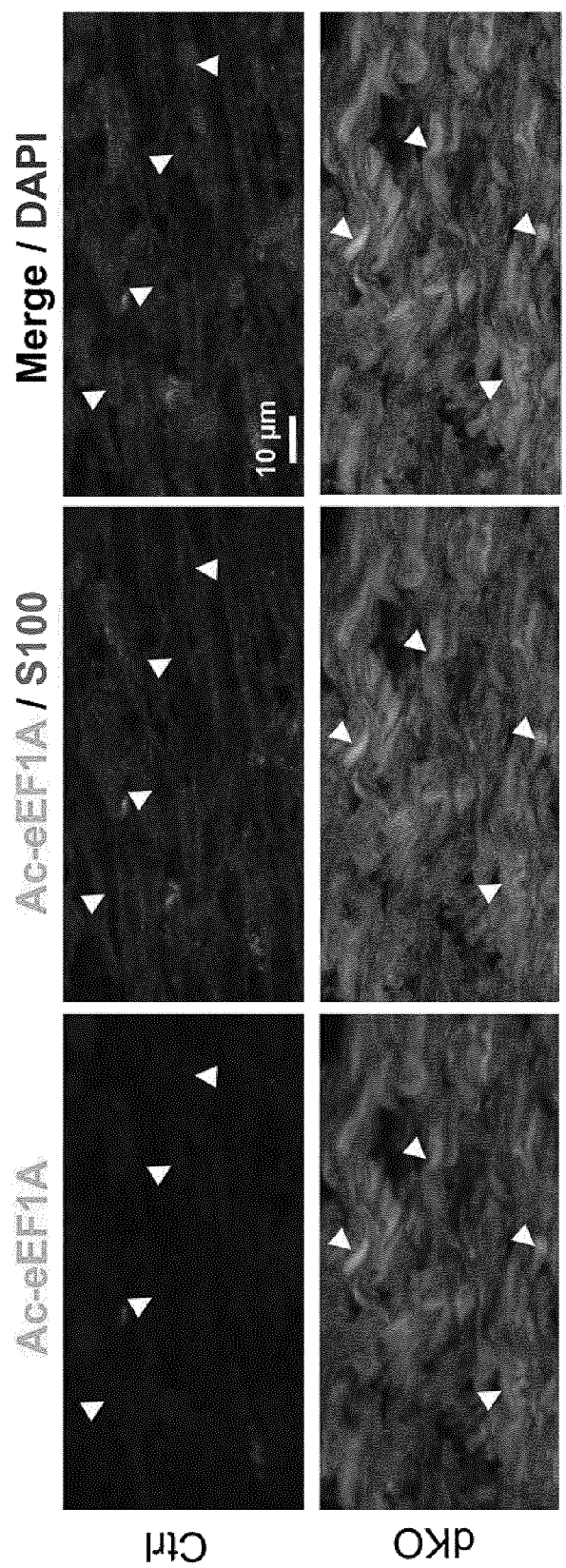
FIG. 1 shows immunofluorescence of acetylated eEF1A (Ac-eEF1A, left images), acetylated eEF1A and S100 proteins (center images) and the combined fluorescence of DAPI, acetylated eEF1A and S100 proteins (right side images), in sciatic nerve preparations obtained from four-day old control mice (top row) and HDAC1/2 conditional (Schwann cell-specific) knockout mice (dKO). The bottom left image shows accumulation of acetylated eEF1A in the knock-out mice, demonstrating that HDAC1/2 deacetylate eEF1A during developmental myelination.

Hereinafter, preferred embodiments of the device of the invention are described, in order to illustrate the invention, without any intention to limit the scope of the present invention.

DETAILED DESCRIPTION OF THE PREFERRED EMBODIMENTS

The present invention relates to activators of HDAC (histone deacetylase) 1 or 2, of HDAC1/2 enzymatic activity and/or HDAC1/2 expression and their medical uses, as well as methods of treatment and/or prevention comprising administering the activators. The invention also relates to methods of screening for candidate agents that are suitable in the treatment and/or prevention of a demyelinating condition.

For the purpose of the present invention, an "activator of HDAC1/2", an "activator of HDAC1/2 activity" and/or an "activator of HDAC1/2 expression" is an agent that increases the enzymatic activity of HDAC1 and/or HDAC2, and/or which increases expression of HDAC1 and/or HDAC2, in particular in cells selected from Schwann cells, other glia cells, in particular oligodendrocytes, and nerve cells. Said enzymatic activity is preferably the deacetylase activity of HDAC1 and/or HDAC2. Allosteric modulators are also considered as an HDAC1/2 activator, in as far as they contribute to increasing the activity and/or the expression of HDAC1 and/or HDAC2.

In an embodiment, the activator increases HDAC1 and/or HDAC2 deacetylase activity and/or expression in vivo and/or in vitro. Deacetylase activity and/or expression in vitro includes activity and/or expression determined in living cells, for example in primary Schwann cell cultures, or in cells in a sample taken from an organism, for example taken from an organism before determining said activity and/or expression. The HDAC1/2 used in in vitro assays may or may not be recombinant. Deacetylase activity in vitro also includes activity determined in a sample containing an isolated polypeptide susceptible of exhibiting HDAC1 or HDAC2 deacetylase activity, for example a sample comprising isolated and/or recombinant HDAC1/2.

HDAC1 and HDAC2 are two different types of deacetylases of class I histone deacetylases. They have partially the same and partially different substrates. It has been observed that one of these HDACs can compensate for the loss of activity of the other. For example, in case of knock out of HDAC2, HDAC1 was observed to at least partially assume the function of HDAC2. Therefore, the two HDAC members are generally mentioned together in the present specification. In a preferred embodiment, said HDAC is HDAC2. In an embodiment, said activator is at least an activator of HDAC2, and optionally also an activator of HDAC1. In case of activators of only one of HDAC1 or HDAC2, activators of HDAC2 are preferred. In an embodiment, said activator is an activator of HDAC2 or of both HDAC1 and HDAC2. Preferably, said activator is not an activator of HDAC1 exclusively, without being an activator of HDAC2.

HDAC1/2 activators have been reported in the literature. In particular, WO2010/011318 A2, published on Jan. 28, 2010 and filed on Jul. 23, 2009 under application number PCT/US2009/04267, discloses activators of HDAC1 and other HDACs. WO2010/011318 is entirely and expressly incorporated herein by reference. The HDAC activators disclosed starting on page 2, line 26 through page 10, line 4 are expressly incorporated herein by reference. Furthermore, flavonoids as disclosed on page 21, line 17 through page 21, line 26 are expressly incorporated herein by reference. Further HDAC activators disclosed on page 21, line 27 through page 48, line 5 are expressly incorporated herein by reference. The definitions of terms in these paragraphs given elsewhere in the specification of WO2010/011318 are also expressly incorporated herein by reference. Such definitions are given, for example, on page 50, line 6 through page 63, line 22 and are expressly incorporated herein by reference. HDAC1 activators disclosed in Table 5 (pages 114-115) of WO2010/011318 are also expressly incorporated herein by reference. Furthermore, HDAC activators and embodiments as disclosed in the claims of WO2010/011318 and as defined in the specification are expressly incorporated herein by reference.

In an embodiment, the HDAC1/2 activator is selected from the group consisting of: an alkaloid compound, an iron chelator, deferoxamine, a flavonoid, for example ginkgetin K, a compound comprising a catechol moity, Chembridge 5104434, sciadopilysin, tetrahydrogamboic acid, TAM-11, gambogic acid, or a derivative thereof, LY235959, CGS19755, SKF 97541, etidronic acid, levonordefrin, methyldopa, ampicillin trihydrate, D-aspartic acid, gamma-D-glutamylaminomethylsulfonic acid, phenazopyridine hydrochloride, oxalamine citrate salt, podophyllotoxin, (+−)-4-amino-3-(5-chloro-2-thienyl)-butanoic acid, (RS)-(tetrazol-5-yl) glycine, or RH-SKF-81297. The structures of the aforementioned compounds are disclosed in WO2010/011318, and are incorporated herein by reference, in particular page 44, line 4 through page 18, line 5.

In an embodiment, the HDAC1/2 activator is an alkaloid compound. Preferably, the HDAC1/2 activator is a xanthine compound. In an embodiment, the HDAC1/2 activator is a xanthine compound as defined in US2003/0134865, which is entirely and expressly incorporated herein by reference. In an embodiment, the xanthine compound is xanthine, a derivative of xanthine or a salt of any one of the aforementioned. In an embodiment, xanthine compound is alkylated xanthine, preferably a methylated xanthine (methylxanthine). Said alkylated xanthine may be mono-, di-, or trialkylated xanthine, for example. In an embodiment, said HDAC1/2 activator is a dialkylated xanthine, for example a dimethylxanthine.

In an embodiment, the xanthine compound is selected from the group consisting of theophylline, caffeine, acepifylline (etaphylline), bamifylline, bufylline, cafaminol, cafedrine, diprophylline, doxofylline, enprofylline, etamiphylline, etofylline, proxyphylline, suxamidofylline, theobromine, paraxanthine, 8-chlorotheophylline, 8-phenyltheophylline, IBMX (1-Methyl-3-(2-methylpropyl)-7H-purine-2,6-dione), DMPX (3,7-dimethyl-1-propargylxanthine), CPX (8-Cyclopentyltheophylline), DPCPX (8-Cyclopentyl-1,3-dipropylxanthine or PD-116,948), a salt of any one of the aforementioned, an alkylated form of any one of the aforementioned and combinations comprising two or more of the aforementioned compounds. Salts include pharmaceutically acceptable salts.

In a preferred embodiment, the HDAC1/2 activator is theophylline.

In an embodiment, the HDAC1/2 activator is selected from the group consisting of: a xanthene compound, xanthydrol, xanthone, and combinations of two or more of the aforementioned.

In an embodiment, the HDAC1/2 activator is theophylline or a pharmaceutically acceptable salt thereof.

In an embodiment, the HDAC1/2 activator is for treating and/or preventing a disease or condition associated with demyelination. Preferably, the HDAC1/2 activator is used for accelerating, increasing and/or promoting myelination and in particular remyelination in such diseases and conditions.

In an embodiment, the HDAC1/2 activator is for accelerating regeneration of nerve cells of the peripheral nervous system (PNS) and/or of the central nervous system (CNS).

In an embodiment, the HDAC1/2 activator is for treatment, prophylaxis and/or for increasing remyelination in the context of:
(i) demyelination due to traumatic injury of the peripheral nervous system;
(ii) demyelination due to Multiple Sclerosis;
(iii) peripheral neuropathies where demyelination occurs, such as subtypes of the Charcot-Marie Tooth diseases where gene mutation leads to hypomyelination or demyelination, Waardenburg syndrome, Guillain-Barré syndrome, chronic inflammatory demyelinating polyneuropathy or neurofibromatosis;
(iv) demyelination due to aging, diabetes or toxic agents;
(v) demyelination and/or hypomyelination due to other diseases of the CNS, such as Acute disseminated encephalomyelitis, transverse myelitis, Leukodystrophy, Central pontine myelinolysis, Glioma, schizophrenia;
(vi) demyelination after traumatic lesion of the CNS.

In an embodiment, the HDAC1/2 activator of the invention is provided, for promoting, increasing and/or accelerating remyelination of nerve cells of the PNS after lesion, and which activator is administered at the earliest 5 days after occurrence of the lesion, preferably at the earliest 7 days after lesion. It has previously been shown that HDAC2 activity immediately after a lesion affecting nerve cells results in an upregulation of Oct6, which slows down the upregulation of cJun. cJun in turn induces the conversion of mature Schwann cells into repair Schwann cells and thereby promotes axonal regrowth. Therefore, in case of a lesion of peripheral nerves, HDAC2 activity immediately after a lesion negatively impacts axonal regrowth and should preferably be avoided. However, the present inventor has shown that after the conversion of mature Schwann cells into repair Schwann cells, HDAC2 activity contributes to remyelination. Therefore, the invention provides administering an HDAC1/2 activator with some delay after damage to the PNS. This delay is preferably 5 days, more preferably 7 days, and most preferably 8 or 9 days (days post lesion, dpl). In accordance with an embodiment, the HDAC1/2 activator is administered during the period of 5 to 25 dpl, preferably 6 to 20 dpl, more preferably 7 to 17 dpl and most preferably 9 to 15 dpl.

In another embodiment, the HDAC1/2 activator of the invention is provided, for promoting, increasing and/or accelerating remyelination of nerve cells of the CNS after lesion or after a demyelinating event. In an embodiment, the invention provides the HDAC1/2 activator for increasing and/or accelerating remyelination of nerve cells of the CNS after an attack to glia cells, in particular oligodendrocytes. For treating any demyelinating condition or event occurring in the CNS, the HDAC1/2 activator is preferably administered rapidly and/or immediately after the demyelinating event. Furthermore, in case of a demyelinating condition in the CNS, the HDAC1/2 activator may be administered at time of diagnosis or rapidly thereafter. In an embodiment, the HDAC1/2 activator is administered within 30 days from a demyelinating event in the CNS or said diagnosis, more preferably within 15 days, even more preferably within 9 days and most preferably within 7 days after the occurrence of a demyelinating event or after the diagnosis of a demyelinating event or condition. In other embodiments, the HDAC1/2 activator is administered within 6 days from a demyelinating event in the CNS or said diagnosis, more preferably within 4 days, even more preferably within 2 days and most preferably within 1 day.

The present invention also relates to methods of screening. In an embodiment, the method of screening comprises the step of assessing, in an in vitro sample exposed to the candidate compound, whether HDAC1/2 activity and/or expression is increased compared from a sample which is devoid of said candidate compound. Said in vitro sample may comprise cells or an isolated and/or recombinant polypeptide exhibiting HDAC1/2 activity. Said polypeptide is preferably human or animal HDAC1, or human or animal HDAC2, and/or said cells preferably express human or animal HDAC1, or human or animal HDAC2. In some embodiments, said polypeptide and/or said cells comprise HDAC1 or 2 from a vertebrate animal, preferably from a mammal, such as a rodent. Preferably, said sample comprises cells that have been taken previously from a subject, preferably before the step of assessing HDAC1/2 activity and/or expression.

In an embodiment, the method for screening comprises the step of evaluating the capacity of a candidate agent to increase the HDAC1/2 activity and/or expression, wherein presence of capacity to increase HDAC1/2 activity and/or expression indicates that said candidate agent is an agent suitable for the treatment of said diseases and for promoting myelination.

HDAC1/2 activity and/or expression may be determined in any suitable way. In vitro, the HDAC1/2 activity is preferably determined by assessing the HDAC1/2 deacetylase activity with respect to a suitable substrate. In an embodiment, the substrate comprises a marker molecule, for example marker peptides, suitable for assessing, preferably quantifying, the consumption of the substrate and/or the production of the product. The term "substrate" for the present invention encompasses dipeptides, tripeptides, oligopeptides and polypeptides as well as derivatives thereof.

In an embodiment, said substrate is or comprises a Eukaryotic elongation factor (eEF) peptide, preferably a eEF1A peptide, more preferably a eEF1A1 peptide. Said peptide may be comprised in the sample naturally, for example expressed by cells contained in the sample, or may be added in the form of an isolated and/or recombinant polypeptide. Said eEF peptide is preferably of human or animal origin, preferably of vertebrate origin, most preferably said eEF peptide is a mammal eEF, such as a human or rodent eEF.

Assessing or determining said HDAC1/2 activity preferably refers to one or more activities related to the qualitative finding of presence or absence of an enzymatic activity as specified, the quantitative approximation of such activity, for example in terms of rate of product consumption, relative comparison of activities, and/or also the quantitative measurement of such activity, for example.

For example, suitable marking systems could be substrates in which deacetylation induces the loss of fluorescence activated energy transfer (FRET) between suitable donor/acceptor pairs that would be added on suitable sites within the substrate which are preceding and following the cleavage site (for example the N- and C-terminus of a substrate peptide). This would allow to assess a loss of FRET upon cleavage because of the resulting separation of acceptor and donor moieties. A similar principle could be used to change (for example, destroy or obtain) any physical, chemical, or biological (e.g. enzymatical) property depending on proximity of two parts for functionality. For example, it is possible for a marker of HDAC1/2 activity to obtain measurable physical, chemical or biological property, such as fluorescence, enzymatical or other biological activity through deacetylation of the substrate.

In an embodiment, expression of HDAC1/2, preferably HDAC2 may be assessed by Western blot, preferably following immunoprecipitation with an antibody capable of binding to the starting product or an end product of HDAC1/2 activity (e.g. Acet-eEF1A1 or eEF1A1), or an antibody binding to another protein connected to said starting and/or end product of HDAC1/2 activity.

In an embodiment, HDAC1/2 activity is assessed by quantifying the acetylated or deacetylated substrate of HDAC1/2. This may be made, for example, by immunofluorescence, for example by exposing the substrate to an antibody specific for either the acetylated or the deacetylated variant of the substrate.

In an embodiment, the step of assessing the capacity of a candidate agent to increase the HDAC1/2 activity and/or expression comprises: exposing a sample comprising a polypeptide exhibiting HDAC1/2 deacetylase activity to a said candidate compound, and, determining whether in said sample said HDAC1/2 deacetylase activity and/or expression is increased compared to a comparative sample devoid of said candidate compound.

The present invention comprises methods of treatment and/or prophylaxis, said methods comprising administering an HDAC1/2 activator, including compound increasing the expression of HDAC1/2. In these methods, the compound is preferably administered in a form as appropriate for the particular activator. Oral and parenteral administrations are preferred for administering the HDAC1/2 activator. For example, theophylline may be administered orally or parenterally. Preferably, a therapeutically and/or pharmaceutically effective amount of the activator is administered. Preferably, the activator is administered together with a pharmaceutically acceptable carrier. Preferably, the HDAC1/2 activator is administered in the form of a pharmaceutical composition. The invention also provides pharmaceutical compositions for treatment and/or prophylaxis of the diseases, conditions and/or disorders disclosed in the present specification.

In some aspects and embodiments, the invention provides the HDAC1/2 activator in combination with an anti-inflammatory agent, for treating one or more conditions specified in this specification. Preferably, the HDAC1/2 activator and the anti-inflammatory agent are for treating and/or preventing multiple sclerosis (MS).

For the purpose of the present specification, the HDAC1/2 activator is not considered as an anti-inflammatory agent, as it is administered for its capacity of promoting remyelination.

As indicated in the introduction, current treatments of MS involve administering an anti-inflammatory agent. While these treatments prevent auto-immune attacks or increase the time gap between such attacks, they do not assist in regeneration or remyelination of the lesions. With disease progression and increasing age, the regeneration of the attacked tissue slows down and eventually there is no complete regeneration anymore, resulting in irreversible damage to tissue of the CNS due to the attacks by immune cells.

The present invention provides a combinatorial treatment, which synergistically treats the condition such as MS by preventing the attacks against nerve cells and promoting remyelination and regeneration in case an attack takes place. The combinatorial treatment results in improved treatment outcome and/or prolongs patient life and neural functions.

In an embodiment, said anti-inflammatory agent is a corticosteroid, preferably a glucocorticoid.

In an embodiment, the corticosteroid is selected from cortisol ($C_{21}H_{30}O_5$), corticosterone ($C_{21}H_{30}O_4$), cortisone ($C_{21}H28O_5$) and aldosterone ($C_{21}H28O_5$).

In an embodiment, said anti-inflammatory agent is a protein, preferably selected from cytokines, such as interferons, and antibodies, preferably monoclonal antibodies.

Preferred anti-inflammatory agents that may be administered in combination with the HDAC1/2 activator may be selected from the group consisting of Interferon β1a (CAS number: 145258-61-3), Glatiramer acetate (CAS number: 147245-92-9), Mitoxantrone (CAS number: 65271-80-9), Natalizumab (CAS number: 189261-10-7), Alemtuzumab (CAS number: 216503-57-0), Daclizumab (CAS number: 152923-56-3), Ocrelizumab (CAS number: 637334-45-3), Cladribine (CAS number: 4291-63-8), Fingolimod (CAS number: 162359-55-9), Dimethyl fumarate (CAS number: 624-49-7), and Ofatumumab (CAS number: 679818-59-8), and corticosteroids.

In accordance with the invention, the HDAC1/2 activator and anti-inflammatory agent may be administered simultaneously and/or sequentially. The invention provides a single pharmaceutical composition comprising both, the HDAC1/2 activator and the anti-inflammatory agent.

In another embodiments, the invention provides administration of separate pharmaceutical composition, a first pharmaceutical composition comprising the HDAC1/2 activator and optionally at least one pharmaceutically acceptable carrier, and a second pharmaceutical composition comprising the anti-inflammatory agent and optionally at least one pharmaceutically acceptable carrier.

The administration routes of said first and second pharmaceutical compositions may be the same or different. In an embodiment, the first and second pharmaceutical compositions are for oral, nasal or buccal administration, in another embodiment they are both for parenteral administration.

In an embodiment, the second pharmaceutical composition comprising the anti-inflammatory agent is for parenteral administration, e.g. intravenous administration, and the first pharmaceutical composition is for oral, nasal and/or buccal administration.

While certain of the preferred embodiments of the present invention have been described and specifically exemplified above, it is not intended that the invention be limited to such embodiments. Various modifications may be made thereto without departing from the scope and spirit of the present invention, as set forth in the following claims. Herein below, examples of the invention are disclosed. These examples are for illustration only and are not intended to limit the scope of the present invention.

EXAMPLES

Example 1

Identification of the deacetylation target of HDAC1/2

It was previously found that the two highly homologous histone deacetylases HDAC1 and HDAC2 (HDSC1/2) were robustly upregulated in Schwann cells (myelinating glia of the peripheral nervous system) already one day (for HDAC2) after a sciatic nerve crush lesion in adult mice (ref. 1). It was shown that ablation of these two HDACs in adult Schwann cells impairs remyelination after a sciatic nerve crush lesion (ref. 1) and that this HDAC1/2-dependent mechanism occurs already at one day post lesion (ref. 1). To identify the direct target of HDAC1/2 responsible for their function during the remyelination process, the inventor treated adult mice with the HDAC1/2 inhibitor Mocetinostat or its vehicle immediately after a sciatic nerve crush lesion and collected sciatic nerves 24 h later.

Materials and Methods

Sciatic nerve crush lesions were carried out in adult mice (3-4 month old) with the following procedure: Isoflurane (3% for induction, 1.5-2% for narcosis during operation) was used for anesthesia. For analgesia, 0.1 mg/kg buprenorphine (Temgesic; Essex Chemie) was administered by i.p. injection 1 h before lesion and 12 hours after the operation. An incision was made at the height of the hip and the sciatic nerve was exposed on one side. The nerve was crushed (5×10 sec with crush forceps: Ref FST 00632-11) and the wound was closed using Histoacryl Tissue Glue (BBraun). After the operation, mice were wrapped in paper towels and placed on a warming pad until recovery from anesthesia. The HDAC1/2 inhibitor Mocetinostat (Selleckchem) or its vehicle was injected in the pelvic cavity at 10 mg/kg after wound closure and mice were sacrificed 24 h later.

For immunoprecipitation (IP), the injured sciatic nerve was collected from the lesion site to around 12 mm distal to the lesion site (region where the nerve splits into the three branches of tibial, sural and common peroneal nerves). After perineurium removal, sciatic nerves were frozen in liquid nitrogen, pulverized with a chilled mortar and pestle, lysed in radioIP assay (RIPA) buffer (10 mM Tris/HCl, pH 7.4, 150 mM NaCl, 50 mM NaF, 100 mM NaVO4, 1 mM EDTA, 0.5% wt/vol sodium deoxycholate, and 0.5% Nonidet P-40) for 15 min on ice, and centrifuged to pellet debris. Supernatants were collected and pre-cleared for 1 h with 30 gl protein A/G PLUS agarose beads (Santa Cruz Biotechnology). One milliliter of cleared lysates was rotated overnight at 4° C. with immunoprecipitating antibodies: 2 gg of Acetyl-lysine (rabbit, Abcam, cat. # ab21623) or GFP (rabbit, Abcam, cat. # ab290) antibodies were used per nerve and 2 nerves were used per IP. Rabbit anti-GFP antibody was used as negative control IP. Forty microliters of agarose beads were added, and samples were rotated for 1h at 4° C. Immunoprecipitates were pelleted, washed four times with RIPA buffer, and another four times with 50 mM Tris buffer, pH 6.8.

Proteins from these agarose pull-downs were then in-solution digested with 100 ng sequencing grade trypsin (Promega) for 6 hours at 37° C. after the following treatment: the dry beads were suspended in 30 µl of 8 M urea in 50 mM Tris/HCl, pH 8.0, followed by reduction of the proteins with 3 µl 0.1 M DTT for 30 min at 37° C. and alkylation by addition of 3 µl 0.5 M iodoacetamide for 30 min at 37° C. in the dark, and urea dilution to 2 M by addition of 20 mM Tris/HCl pH 8.0 containing 2 mM CaCl2. Digestion was stopped by adding 1/20 of volume of 20% (v/v) TFA. An aliquot of 5 µl of each digest was analyzed by LC-MS/MS on an EASY-nLC1000 chromatograph connected to a QExactive HF mass spectrometer (Thermo Fisher Scientific) using three replicate injections in case of the in-solution digests. Peptides were trapped on a Pepmap100 Trap C18 300 gm×5 mm (Thermo Fisher Scientific) and separated by backflush onto the analytical column (C18 Aqua Magic, 3 µm, 100 Å, 75 gm×150 mm) with a 20 or 40 min gradient from 5% to 40% solution B (95% acetonitrile, 0.1% formic acid) at a flow rate of 300 nl/min. Full MS (resolution 60000, automatic gain control target of 1 e6, maximum injection time of 50 ms) and top 15 MS/MS (resolution 15000, target of 1e5, 110 ms) scans were recorded alternatively in the range of 400 to 1400 m/z, with an inclusion window of 1.6 m/z, relative collision energy of 27, and dynamic exclusion for 20 s.

Fragment spectra data was converted to mgf with ProteomeDiscoverer 2.0 and peptide identification made with EasyProt software, and processed with MaxQuant/Andromeda version 1.5.0.0 (MQ) searching against the forward and reversed UniprotKB SwissProt mouse protein database (Release 2014_01) with the following parameters: parent mass error tolerance of 10 ppm, trypsin cleavage mode with 2 missed cleavages, static carbamidomethylation on Cys, variable oxidation on Met and acetylation on Lys. Based on reversed database peptide spectrum matches, a 1% false discovery rate (FDR) was set for acceptance of target database matches.

Results

Mass spectrometry analyses by Protein Match Score Summation on the nerves of mice treated with Mocetinostat revealed increased abundance of eukaryotic elongation factor (eEF)1A1 peptides (and of other peptides such as histone peptides, which are known HDAC targets) compared to vehicle, after immunoprecipitation with an anti-acetyl-lysine antibody, suggesting that HDAC1/2 deacetylate eEF1A1 after lesion.

Example 2

HDAC1/2 and eEF1A1 during Development

In order to determine whether acetylated eEF1A1 is also deacetylated by HDAC1/2 during developmental myelination, HDAC1/2 was specifically ablated in Schwann cells during embryonic development at the Schwann cell precursor stage by crossing Hdac1 and Hdac2 foxed mice with Dhh-Cre mice until obtention of Dhh-Cre$^{+/-}$, HDAC1$^{flox/flox}$, HDAC2$^{flox/flox}$, generating homozygous HDAC1/2 double knockout mice (dKO) in Schwann cells. Dhh-Cre$^{-/-}$ littermate mice were used as control (ctrl). It was previously shown that HDAC1/2 are strongly upregulated after birth in mouse Schwann cells when the myelination process starts (ref. 2).

Materials and Methods

To generate HDAC1/2 conditional knockout mice, mice homozygous for Hdac1 and Hdac2 foxed alleles (ref. 3) were crossed with mice expressing Cre recombinase under control of the Dhh promoter (Dhh-Cre, ref. 4) to ablate HDAC1 and HDAC2 in Schwann cell precursors. Genotypes were determined by PCR on genomic DNA.

For immunofluorescence, P4 mouse pups were killed by decapitation and their sciatic nerves were fixed in situ with 4% paraformaldehyde (PFA) for 10 min, dissected, embedded in O.C.T. Compound (VWR chemicals), and frozen at −80° C. Sciatic nerve cryosections (5 μm thick) were first incubated with acetone for 10 min at −20° C., washed in PBS/0.1% Tween 20, blocked for 30 min at room temperature (RT) in blocking buffer (0.3% Triton X-100/10% Goat serum/PBS), and incubated with primary antibodies overnight at 4° C. in blocking buffer. Sections were then washed 3 times in blocking buffer and secondary antibodies were incubated for 1 h at RT in the dark. Sections were washed again, incubated with DAPI for 5 min at RT, washed and mounted in Citifluor (Agar Scientific). Primary antibodies: EEF1A-pan (Acetyl-Lys41) (rabbit, 1:200, Assay Biotech, cat. # D12106) and S100 beta antibody [SH-B1] (mouse, 1:300, Gene Tex, cat. # GTX11178). Secondary antibodies were from Jackson ImmunoResearch. Photos were acquired using a Leica TCS SP-II confocal microscope. Z-series projections are shown.

Results

The results of immunofluorescence are shown in FIG. 1. In the column "Acetylated eEF1A", the control does not show any color staining, whereas in the HDAC1/2 knockout mice the regular staining in green shows accumulation of acetylated eEF1A (Ace-eEF1A). In the middle column "Acetylated eEF1A/S100", both images show the red staining by S100 beta antibody, marking Schwann cells. In the right-side images, the staining by DAPI of DNA shows, in addition to the red and green fluorescences where present, in blue the nuclei in the sections.

It is shown here by immunofluorescence using P4 (postnatal day 4) sciatic nerves that acetylated eEF1A (presumably eEF1A1) levels were strongly increased in Schwann cells (S100-positive) of dKO mice compared to Ctrl mice, indicating that HDAC1/2 deacetylate eEF1A (presumably eEF1A1) during developmental myelination in Schwann cells.

Example 3

IP of Sox10 and detection of eEF1A

Sox10 is a transcription factor recruited to the Oct6 SCE HR2 (Oct6 enhancer) in Schwann cells following lesion of peripheral nerves, thereby inducing the upregulation of the transcription factor Oct6. Oct6 upregulation results in the slowing down of the conversion of differentiated Schwann cells into repair Schwann cells after lesion and thereby slows down the process of axonal regrowth, but eventually induces remyelination through the upregulation of the transcription factor Krox20, a major inducer of myelination and remyelination. In addition, Sox10 also upregulates Krox20 expression by direct activation of the Krox20 MSE, a critical enhancer of the Krox20 gene for its activation. The following experiments aim at determining the presence or absence of an interaction between Sox10 and eEF1A1.

Materials and Methods

Purified primary rat Schwann cell cultures were obtained as described (ref. 5). Rat Schwann cells were then grown in proliferation medium: DMEM containing 10% Fetal calf serum (FCS, Gibco), 1:500 penicillin/streptomycin (Invitrogen), 4 μg/ml crude GGF (bovine pituitary extract, Bioconcept), and 2 μM forskolin (Sigma), at 37° C. and 5% CO2/95% air. Schwann cell de-differentiation culture protocol was previously described (ref. 6). Briefly, Schwann cells were first growth-arrested in defined medium (DM, ref. 5) for 8 to 15 h, then 1 mM dbcAMP (Sigma) was added to induce differentiation. Cells were incubated in this medium for another 3 days. The medium was then changed to DM only without dbcAMP, and incubated in this medium for 3 days (differentiation mimicking adult Schwann cell stage). To induce de-differentiation, cells were then changed to proliferation medium and incubated in this medium for 3 days.

Two 15-cm culture plates of confluent de-differentiated rat Schwann cells were used per IP. Cells were either treated with 0.6 μM Mocetinostat (HDAC1/2 inhibitor) or its vehicle for 3 days in de-differentiation medium. Cells were washed with PBS and submitted to subcellular fractionation to separate the nuclear from the cytoplasmic fractions. IPs were then carried out on each fraction nuclear and cytoplasmic, as described above. Immunoprecipitating antibodies: 2.5 μg of eEF1A1 (rabbit, Abcam, cat. # ab157455), Sox10 (rabbit, DCS Innovative Diagnostik-Systeme, cat. # 51058C01) or GFP (rabbit, Abcam, cat. # ab290) antibodies were used per IP. Rabbit anti-GFP antibody was used as negative control IP. Acetylation of eEF1A1 and co-immunoprecipitation of acetylated eEF1A with Sox10 were detected using EEF1A-pan (Acetyl-Lys41) primary antibody (rabbit, Assay Biotech, 1:1000, cat. # D12106). Co-immunoprecipitation of HDAC2 with eEF1A1 was detected using an HDAC2 antibody (mouse, Sigma, 1:1000, cat. # H2663). Light chain-specific goat anti-rabbit-HRP or anti-mouse-HRP secondary antibodies (Jackson ImmunoResearch) were used. Detection was done with Immobilon Western Chemiluminescent HRP Substrate (Millipore). Inputs of the IPs were assayed on lysates used for IPs. GAPDH (mouse, Gene Tex, 1:5000, cat. # GTX28245) and LaminA/C (mouse, Sigma, 1:2000, cat. # SAB4200236) antibodies were used to evaluate the efficiency of cytoplasmic and nuclear fractionation.

Results

Figure 2:
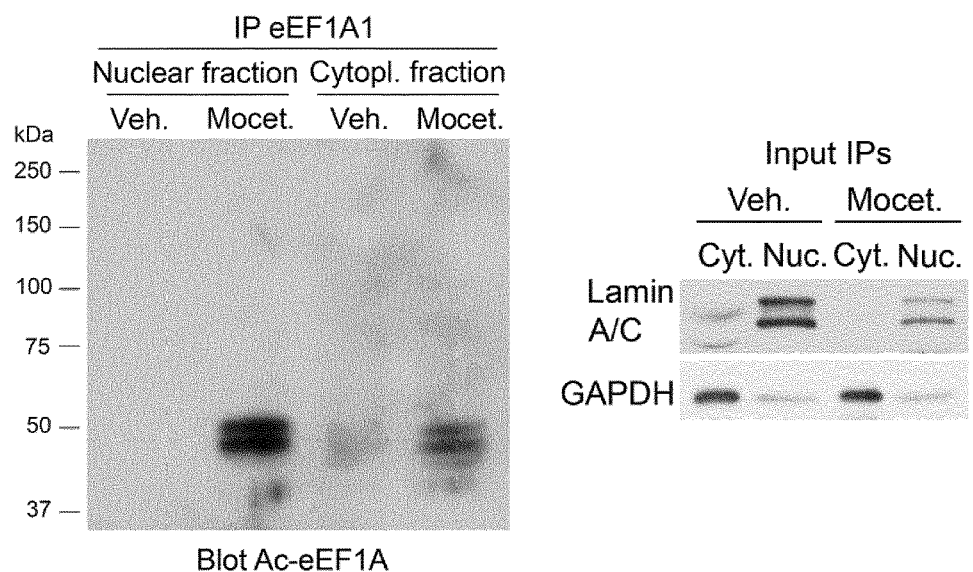
FIGS. 2A, 2B and 2C show WB images of Ace-eEF1A (presumably Ace-eEF1A1) following IP of eEF1A1 (FIG. 2A) or Sox10 (FIG. 2B), or of HDAC2 following IP of eEF1A1 (FIG. 2C), obtained from de-differentiated rat Schwann cells cultured in the presence of the HDAC1/2 inhibitor Mocetinostat or its vehicle. Nuclear and cytoplasmic fractions were separately analysed. Sox10, eEF1A1, GAPDH and Lamin A/C WB (FIG. 2A,B) on cell lysates show the IP inputs. GFP IP is used as a negative control.
Figure 2:
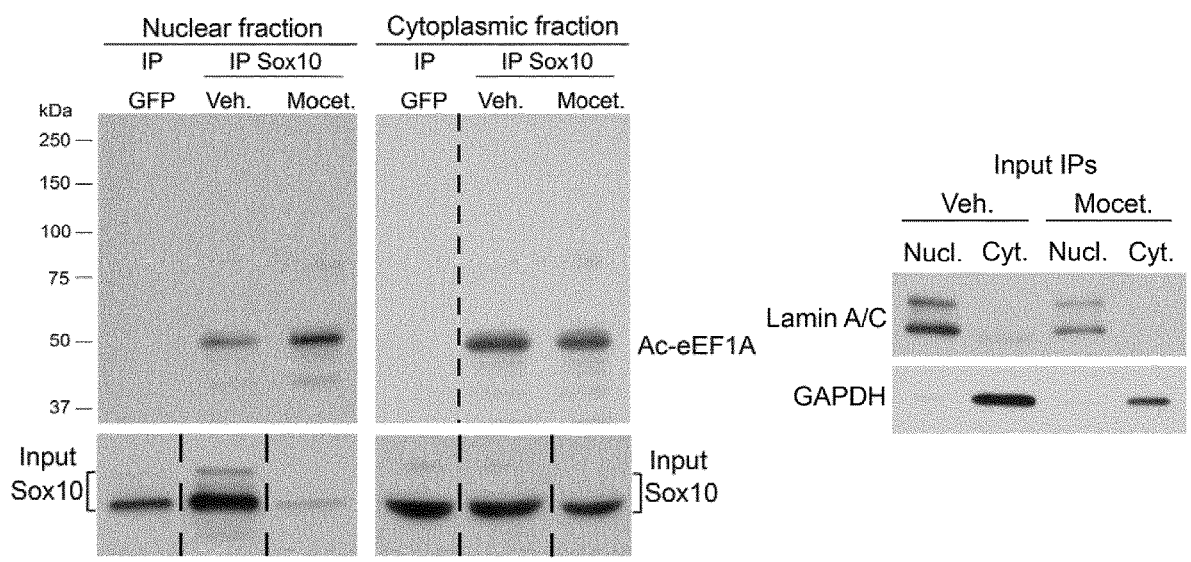
Figure 2:
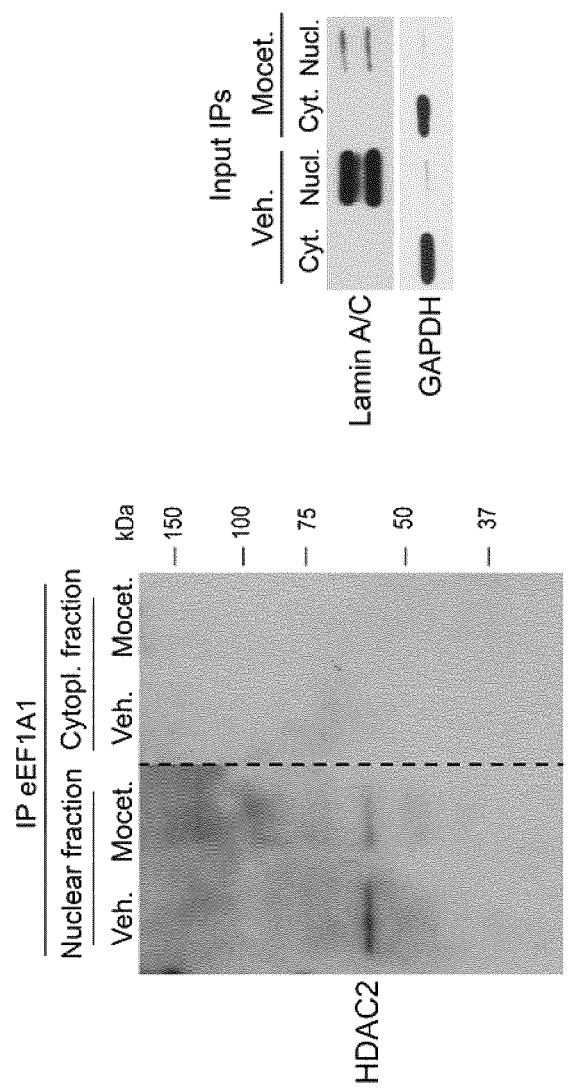

While eEF1A1 is mainly localized in the cytoplasm, it was first found by immunofluorescence in purified rat Schwann cells cultured under de-differentiating conditions in the presence of the HDAC1/2 inhibitor Mocetinostat that acetylated eEF1A is mainly localized in the nucleus, although a fraction is also found in the cytoplasm (data not shown). Here it is shown by subcellular fractionation, immunoprecipitation and Western blot analyses that indeed inhibition of HDAC1/2 activity leads to a strong increase of acetylated eEF1A1 levels, which is predominantly localized in the nucleus of these cells (FIG. 2A). Under these conditions, it was also found that the major transcription factor of differentiation and myelination Sox10 was partially re-localized from the nuclear to the cytoplasmic compartment and that acetylated eEF1A (presumably eEF1A1) co-immunoprecipitated with Sox10 in both compartments (FIG. 2B). This interaction was potentiated by HDAC1/2 inhibition, which also led to a strong decrease of Sox10 expression in the nuclear compartment, suggesting that acetylated eEF1A1 interacts with Sox10 to drag it out of the nucleus. The results also show that HDAC2 co-immunoprecipitates with eEF1A1 in the nucleus (FIG. 2C), most likely to deacetylate it and thereby send it back to the cytoplasm to protect Sox10 from cytoplasmic re-localization and degradation (data not shown).

Example 4

The Effect of Theophylline on HDAC2, Sox10, Krox20 and P0 Expression

Because HDAC1/2 inhibition strongly increases acetylated eEF1A1 levels and leads to Sox10 re-localization to the cytoplasm and to an overall decrease of Sox10 expression levels, the inventor hypothesized that increasing HDAC2 expression and activity may prevent Sox10 re-localization to the cytoplasm and thereby increase Sox10 expression and activity on its target genes Krox20 and myelin protein zero (P0). To enhance remyelination after a sciatic nerve crush lesion, the effect of theophylline was tested, a drug currently used to treat asthma for its bronchodilator properties, and to treat chronic obstructive pulmonary disease due to its ability to increase HDAC2 expression and activity at low doses.

Materials and Methods

Adult mice were treated with intraperitoneal injection of 10 mg/kg/day theophylline or its vehicle from 9 to 13 days post sciatic nerve crush lesion. At 14 days post lesion (dpl) the injured sciatic nerve ("crush") was collected, as well as the same region of the contralateral nerve ("contra") as internal control for each animal. After perineurium removal, sciatic nerves were frozen in liquid nitrogen, pulverized with a chilled mortar and pestle, lysed in RIPA buffer for 15 min on ice, and centrifuged to pellet debris. Supernatants were collected, and protein concentration was determined by Lowry Protein assay (Bio-Rad Laboratories). Sciatic nerves were submitted to SDS-PAGE and analysed by Western blot. Primary antibodies: HDAC2 (mouse, 1:1000, Sigma, cat. # H2663), Sox10 (rabbit, 1:250, DCS Innovative Diagnostik-Systeme, cat. # SI058C01), GAPDH (glyceraldehyde-3-phosphate-dehydrogenase, mouse, 1:5000, Genetex, cat. # GTX28245), P0 (chicken, 1:1000, Ayes Labs, cat. # PZO), Krox20 (rabbit, 1:500, Axxora, cat. # CO-PRB-236P-100). All secondary antibodies were from Jackson ImmunoResearch: light chain-specific goat anti-mouse-HRP (horse radish peroxidase) and goat anti-rabbit-HRP, and heavy chain-specific goat anti-chicken-HRP.

Results

Figure 3:
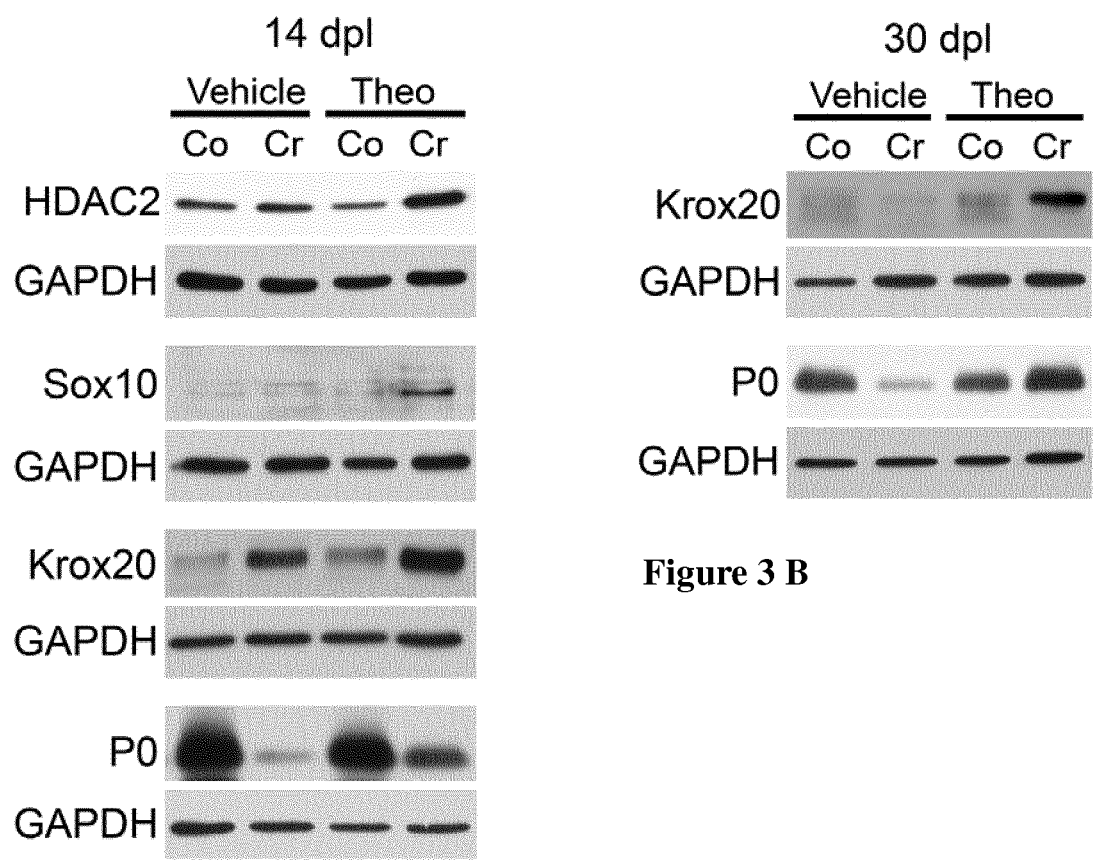
FIGS. 3A and 3B show WB images obtained from lysates of sciatic nerves after crush lesion (Cr) and unlesioned contralateral samples (Co) taken from mice treated with the HDAC2 activator theophylline or its vehicle, at 14 (FIG. 3A) and 30 (FIG. 3B) days post lesion (dpl). The results show that treatment with the activator results in increased levels of HDAC2, Sox10, Krox20 and P0 (myelin protein zero) at 14 dpl (FIG. 3A) and/or 30 dpl (FIG. 3B).

The results show that a short treatment with theophylline for 4 consecutive days starting from 9 days post sciatic nerve crush lesion, when axons have already regrown and when Schwann cells start to re-differentiate to rebuild myelin, resulted indeed in increased HDAC2 expression levels compared to vehicle-treated mice, and also in a high increase of Sox10, Krox20 and P0 at 14 and/or 30 dpl (FIGS. 3A and 3B). This strongly supports the hypothesis that increasing HDAC2 expression and/or activity accelerates the remyelination process after lesion.

Example 5

Theophylline Treatment Increases Sox10 and P0 levels through HDAC2

This example assesses whether theophylline-induced increase of Sox10 and P0 levels is dependent on HDAC2.

Materials and Methods

In P1 control and dKO mice (as described in Example 2), 10 mg/kg theophylline or its vehicle were injected subcutaneously once a day for 3 days. Sciatic nerves were collected at P4. After perineurium removal, sciatic nerves were frozen in liquid nitrogen, pulverized with a chilled mortar and pestle, lysed in RIPA buffer for 15 min on ice, and centrifuged to pellet debris. Supernatants were collected, submitted to SDS-PAGE and analysed by Western blot. Primary antibodies: HDAC2 (mouse, 1:1000, Sigma, cat. # H2663), Sox10 (rabbit, 1:250, DCS Innovative Diagnostik-Systeme, cat. # SI058C01), GAPDH (glyceraldehyde-3-phosphate-dehydrogenase, mouse, 1:5000, Genetex, cat. # GTX28245), P0 (chicken, 1:1000, Ayes Labs, cat. # PZO). Secondary antibodies were from Jackson ImmunoResearch: light chain-specific goat anti-mouse-HRP (horse radish peroxidase) and goat anti-rabbit-HRP, and heavy chain-specific goat anti-chicken-HRP.

Results

Figure 4:
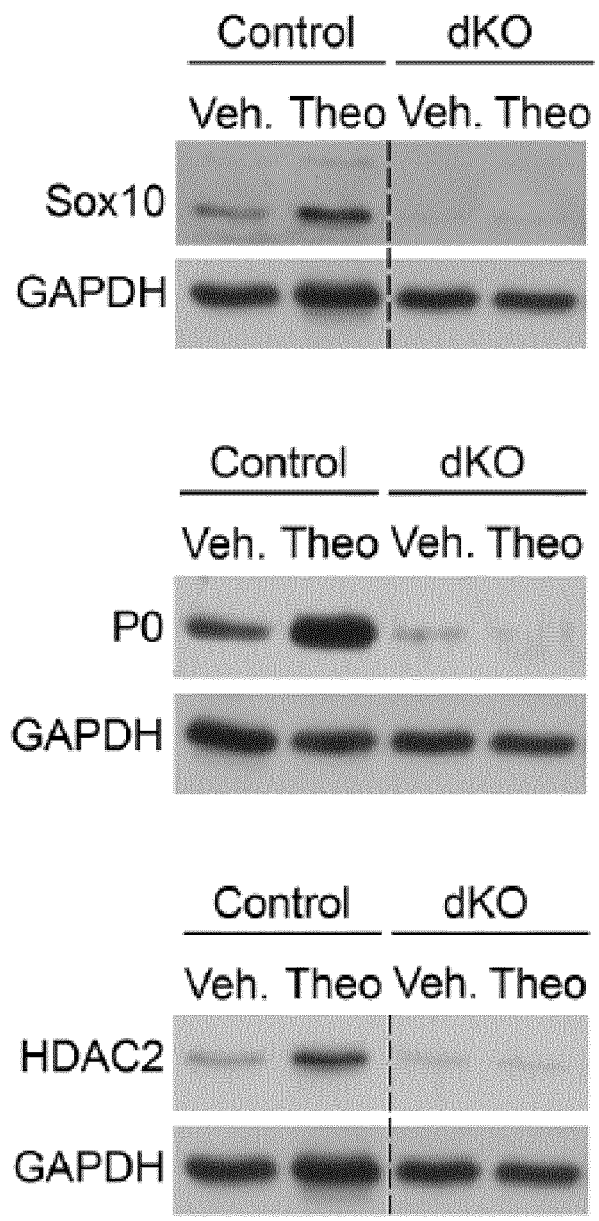
FIG. 4 shows WB images obtained from sciatic nerve lysates of four-day old control mice and HDAC1/2 conditional (Schwann cell-specific) knockout mice (dKO) after treatment with the HDAC2 activator theophylline (Theo) or its vehicle (Veh.) for 3 days (starting at one day after birth). The results show that treatment with the activator leads to increased levels of HDAC2, Sox10 and P0 in control mice, but not in dKO mice.

The results presented in FIG. 4 show that theophylline treatment increases the levels of HDAC2, Sox10 and P0 in control mice, but not in dKO mice where HDAC1 and HDAC2 were ablated specifically in Schwann cells. These data indicate that theophylline induces an upregulation of the promyelinating factor Sox10 and the myelin protein P0 by a mechanism dependent on HDAC2 (and potentially also on HDAC1).

Example 6

HDAC2 Activator Increases Myelin Thickness

This example evaluates the effect of the HDAC2 activator theophylline on myelin thickness of crushed sciatic nerves in the course of remyelination.

Materials and Methods

Adult mice were treated with theophylline or vehicle as described above in Example 4 from 9 to 13 days post sciatic nerve crush lesion. Injured sciatic nerves were collected for morphological analysis by electron microscopy. Briefly, mice were killed with 150 mg/kg pentobarbital i.p. (Esconarkon; Streuli Pharma AG) and sciatic nerves were fixed in situ with 3% paraformaldehyde and 0.15% glutaraldehyde in 0.1 M phosphate buffer, pH 7.4. Fixed tissues were post-fixed in 2% osmium tetroxide, dehydrated through a graded acetone series as described previously (ref. 7), and embedded in Spurr's resin (Electron Microscopy Sciences). Ultrathin cross-sections (90-nm thick) were made, as described (ref. 7). All analyses were done at 5 mm distal to the lesion site. No contrasting reagent was applied. Images were acquired using a Philips CM 100 BIOTWIN equipped with a Morada side-mounted digital camera (Olympus). The g-ratio of at least 50 axons was measured per animal and 3 animals per group (theophylline or vehicle) were used at 14 dpl. At 30 dpl, only 2 animals were used (more animals will be added at 30 days post lesion for statistical analyses).

Results

The results are shown in FIGS. 5, 6A and 6B. The images in FIG. 5 are cross sections of crushed nerves 14 and 30 dpl of vehicle-treated and theophylline-treated mice. In FIGS. 6B, the g-ratio of nerves at 14 dpl and 30 dpl is shown. The g-ratio is a parameter inversely related to the thickness of the myelin layer. FIG. 6B illustrates the parameters d and D used for calculating the g-ratio used in the axis of ordinate in FIGS. 6A. FIG. 6A shows that in animals treated with the HDAC2 activator, the g-ratio is significantly lower, these nerves thus having overall thicker myelin sheaths. FIG. 6A thus confirms statistically the visual impression given by FIG. 5.

Treatment with theophylline resulted in a thicker myelin sheath already at 14 dpl and presumably also at 30 dpl. Myelin sheath thickness was measured by the g-ratio (axon diameter: [axon+myelin] diameter): the lower the g-ratio is, the thicker the myelin sheath is. These results indicate that theophylline treatment leads to faster remyelination after sciatic nerve crush lesion.

Example 7

Functional Recovery by Rotarod and Toe Pinch Test

In this example, it was tested whether theophylline treatment also leads to faster functional recovery after sciatic nerve crush lesion.

Materials and Methods

Adult mice were treated with theophylline or vehicle as described above in Example 4 from 9 to 13 days post sciatic nerve crush lesion (carried out as described above in Example 1). Mice were placed three times on the Rotarod apparatus at a fixed speed of 15 rpm to test balance and motor coordination, at 14 and 30 dpl. The duration of each trial was limited to 600 s, and trials were separated by a 30 min recovery period. Latency to fall from the rotating beam was recorded and the average of the three trials was used for quantification. Recovery of sensory function was tested at 14 and 30 dpl by toe pinch test: each toe of the rear foot on the right side (lesioned side) was pinched with equal pressure applied by the same experimenter using flat tip forceps. Immediate withdrawal was recorded as functional sensitivity of the pinched toe. In case no toe exhibited sensitivity, the same test was applied to toes of the contralateral side (uninjured side), which always resulted in immediate withdrawal. All mice were between 3 and 4 months old. The experimenter was blinded regarding the treatment that mice received.

Results

Figure 7:
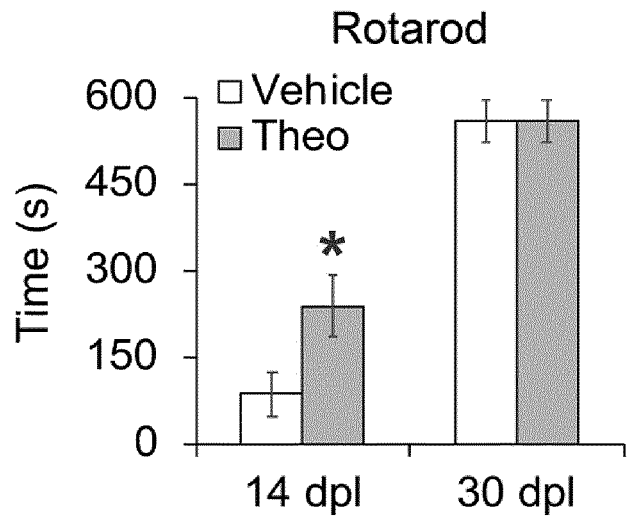
FIG. 7 shows performances of mice at 14 dpl and 30 dpl on a Rotarod, while comparing mice treated with the HDAC2 activator or the vehicle control treatment. At 14 dpl, mice having received the HDAC2 activator exhibit significantly higher motor function and coordination. At 30 dpl, all mice have recovered their motor function and coordination.
Figure 8:
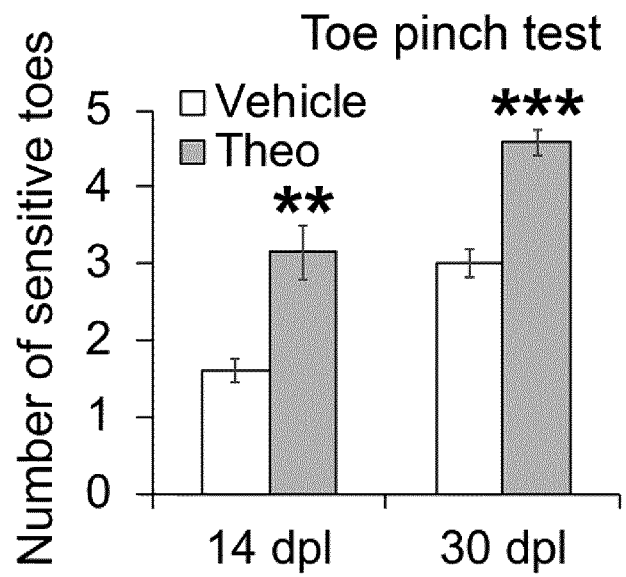
FIG. 8 shows performances of mice at 14 dpl and 30 dpl, respectively, in a toe pinch test. As in FIG. 7, mice treated with the HDAC2 activator are compared to mice having received the vehicle control treatment. At 14 dpl and 30 dpl, mice having received the HDAC2 activator show significantly higher sensory function recovery.

FIGS. 7 and 8 show the results at 14 and 30 dpl of the Rotarod and the Toe pinch test, respectively. These figures show that mice treated with theophylline exhibited higher performances on the Rotarod (motor function and coordination) and had recovered the sensitivity of more toes at 14 dpl, as compared with vehicle-treated mice (FIGS. 7 and 8). The peripheral nervous system can spontaneously regenerate after lesion, and at 30 dpl vehicle-treated mice had already recovered enough of their motor and coordination function to perform as well as theophylline-treated mice on the Rotarod (FIG. 7). However, vehicle-treated mice had not yet recovered their sensory function as well as theophylline-treated mice at 30 dpl (FIG. 8). These data show that theophylline accelerates motor and sensory functional recovery after sciatic nerve crush lesion.

Example 8

Effect of the HDAC2 Activator on Remyelination of Neurons of the Central Nervous System (CNS)

The present example has the purpose of evaluating whether the HDAC2 activator also positively affects the remyelination of neurons in the CNS, after damages resulting in destruction of oligodendrocyte myelin sheaths on axons of neurons. Such damages are characteristic of multiple sclerosis. To model multiple sclerosis demyelinating lesions, the lysolecithin model was used, where focal demyelination occurs within 3 days following lysolecithin injection, due to death of mature oligodendrocytes. In this model, oligodendrocyte precursor cells (OLP) are recruited in the lesion site at 5 dpl and start re-differentiating at 10 dpl. Remyelination starts at 14 dpl (ref. 8).

Materials and Methods

A focal demyelinating lesion was induced in the dorsal funiculus of the spinal cord of adult mice by injection of lysolecithin (1 µl at 1%), as described (ref. 9). This demyelination model is used as a model of multiple sclerosis lesion and is well characterized, the kinetics of demyelination and remyelination being well known. Mice were treated as described above in Example 4 with theophylline or vehicle for 4 days from 9 to 13 days post lysolecithin lesion, when OLP start to re-differentiate to remyelinate demyelinated axons. Mice were killed with 150 mg/kg pentobarbital i.p. (Esconarkon; Streuli Pharma AG) and perfused with 4% PFA. Spinal cords were collected, post-fixed for 2 h in 4% PFA, incubated in 30% sucrose overnight at 4° C., embedded in OCT compound and stored at −80° C. Spinal cords were then processed as sciatic nerves for immunofluorescence, as described in Example 2. Primary antibodies: HDAC2 (rabbit, 1:200, Santa Cruz Biotechnology, cat. # sc-7899), CC1 (mouse, 1:200, Calbiochem/Millipore, cat. # OP80), MBP (rat, 1:500, Serotec, cat. # MCA409S), Sox10 (rabbit, 1:250, DCS Innovative Diagnostik-Systeme, cat. # SI058C01).

Results

Figure 9:
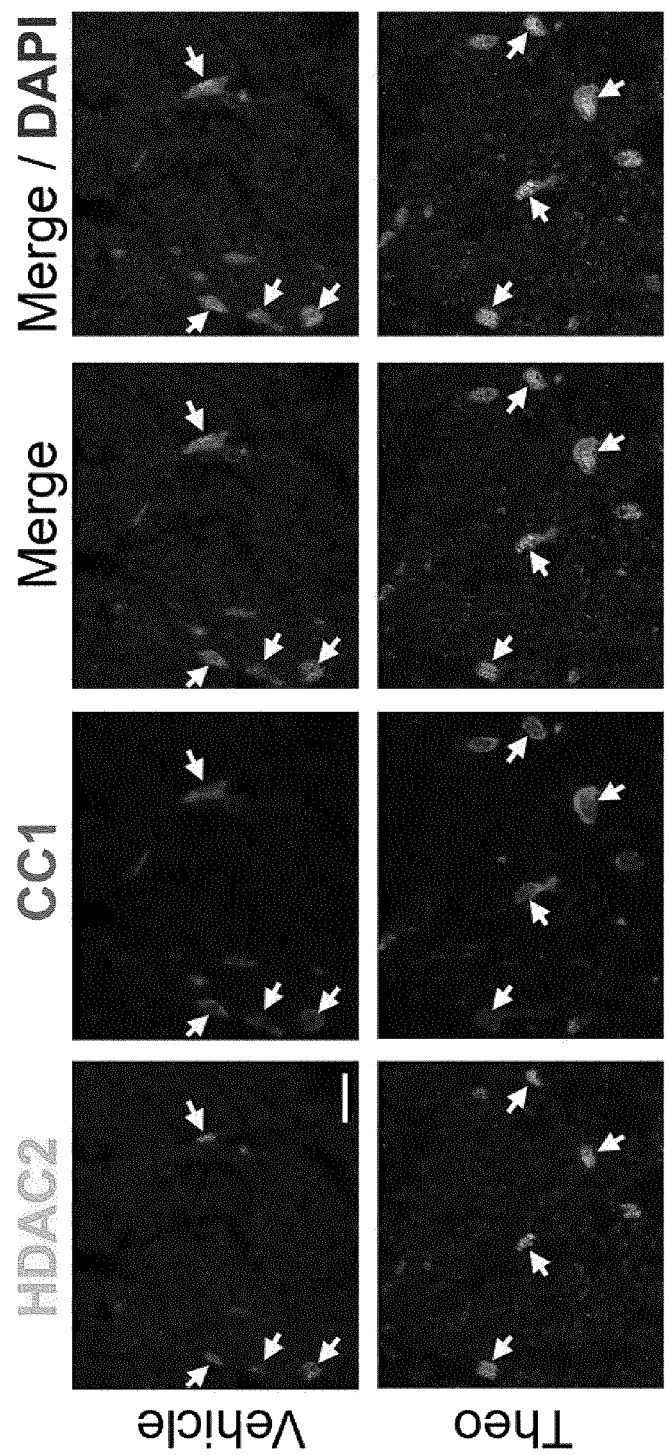
FIGS. 9A and 9B show immuno fluorescence images in the lesion site obtained at 14 dpl from samples of mice that have received a lesion in the dorsal funiculus of the spinal cord. The effect of the HDAC2 activator theophylline (Theo) is compared to control vehicle. The images show higher amounts of HDAC2 in oligodendrocytes (CC1+, FIG. 9A), higher levels of Sox10 and higher myelin content (MBP, FIG. 9B) in the lesion site when the activator was administered.
Figure 9:
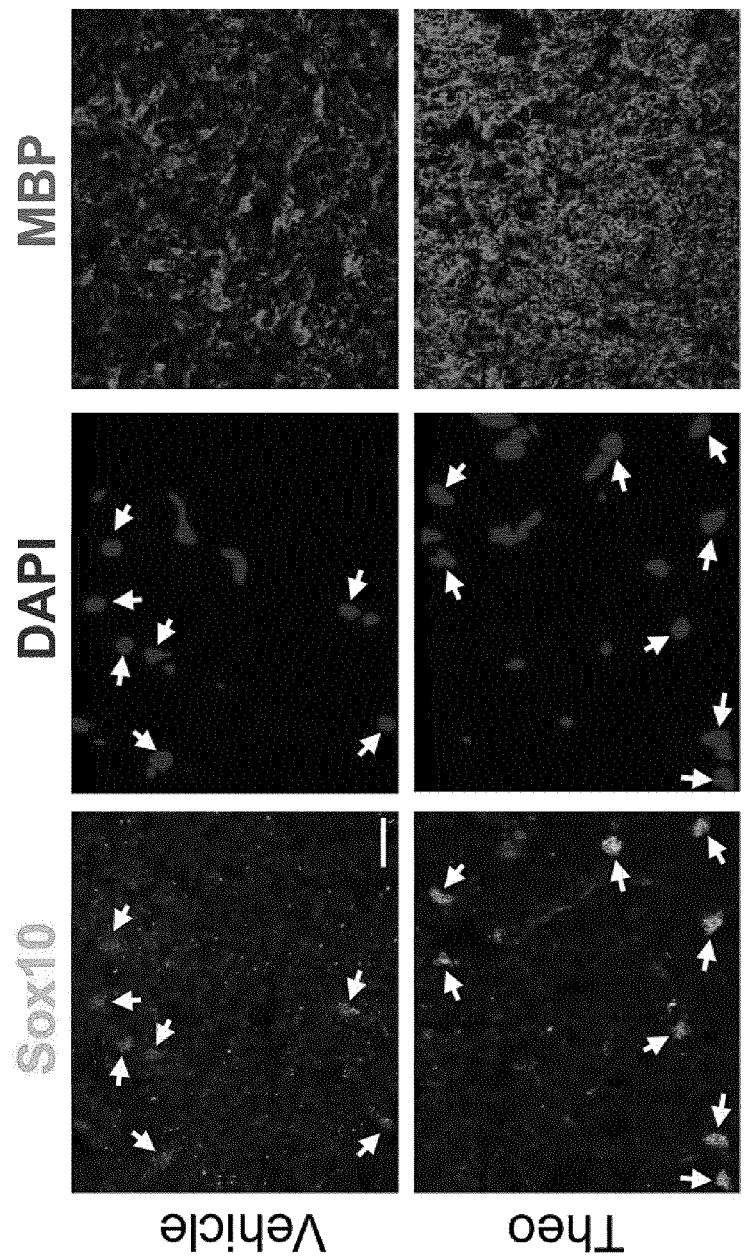

The results are shown in FIGS. 9A and 9B. It is shown here that theophylline treatment strongly increases the levels of HDAC2 expression in the lesion site of the spinal cord, including in differentiated oligodendrocytes (CC1-positive), as compared to vehicle treatment, as can be seen from the green fluorescence in the bottom images on the left and in the middle of FIG. 9A. Only low-intensity green fluorescence is seen in the sample of the top left image of FIG. 9A, where no HDAC2 activator was used. Consistent with the findings in the PNS, theophylline treatment also increases the levels of Sox10 and of myelin basic protein (MBP) in the lesion site at 14 dpl, as compared to vehicle treatment (FIG. 9B). Indeed, the top image in FIG. 9B under "MBP" shows only very little fluorescence, compared to the corresponding image of mice treated with the activator. These data indicate that theophylline is also efficient to increase HDAC2 expression levels and to accelerate remyelination in the CNS after a demyelinating lesion.

Example 9

The HDAC2 Activator Increases Remyelination in the CNS

This example aims at showing the effect of the HDAC2 activator on the myelin recovery in CNS neurons that were subjected to a demyelinating lesion as described in Example 8 above. Furthermore, the effect of an inhibitor on the levels of acetylated eEF1A in the CNS is evaluated.

Materials and Methods

For electron microscopy analyses, adult mice were submitted to a lysolecithin lesion and treated with theophylline or vehicle, as described above in Example 8. Mice were killed at 14 dpl or 30 dpl with 150 mg/kg pentobarbital i.p. (Esconarkon; Streuli Pharma AG) and perfused with 3% PFA and 0.15% glutaraldehyde in 0.1 M phosphate buffer, pH 7.4. Spinal cords were collected and processed as described above in Example 6.

For immuno fluorescence, adult mice were treated with a single intratechal injection of 10 mg/kg Mocetinostat (HDAC1/2 inhibitor) or its vehicle and their spinal cord was collected 24 h after injection. Mice were killed and perfused with 4% PFA and their spinal cord was processed as described above in Example 8. Primary antibody: EEF1A-pan (Acetyl-Lys41) antibody (rabbit, Assay Biotech, 1:1000, cat. # D12106), CC1 (mouse, 1:200, Calbiochem/Millipore, cat. # OP80).

Results

Figure 10:
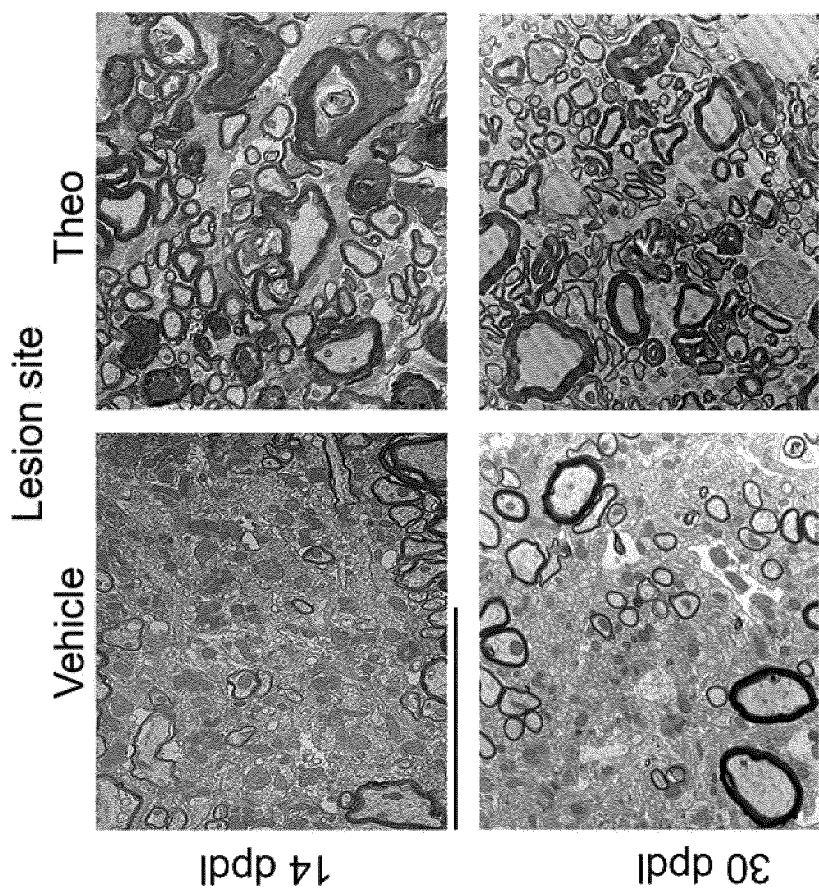
FIG. 10 shows electron microscopy images of spinal cord samples as described for FIGS. 9A-9B at 14 and 30 dpl. When an HDAC2 activator was administered, remyelination of the lesioned spinal cord takes place more rapidly, as can be seen from the image on the right (Theo) compared to left (vehicle).

Consistent with strongly increased MBP levels in the lesion site of theophylline-treated mice, remyelination was also strongly enhanced at 14 and 30 dpl, as compared with vehicle-treated mice, indicating that theophylline treatment also accelerated remyelination of the CNS in the context of demyelinating lesions. In FIG. 10, the right images show more remyelinated (dark) axons, compared to the left images.

Figure 11:
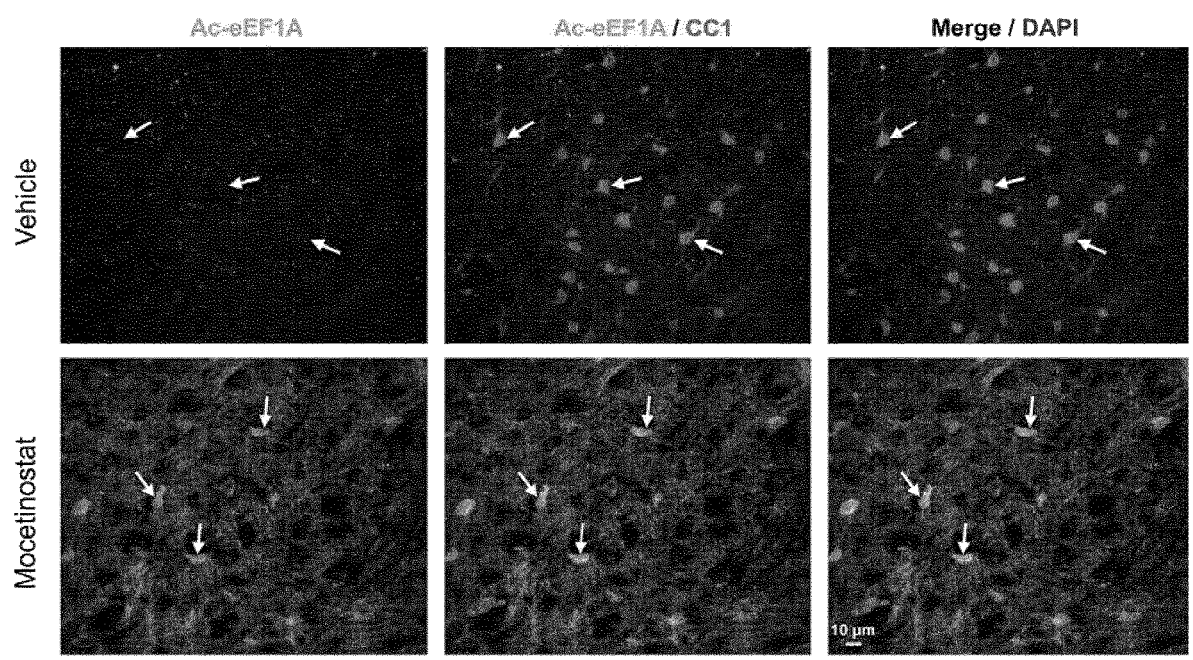
FIG. 11 shows immunofluorescence images obtained from the spinal cord samples of mice treated with the HDAC1/2 inhibitor Mocetinostat (bottom images) or with vehicle control (top images). The image in the left column show that the inhibitor results in accumulation of Ace-eEF1A in the nuclei of oligodendrocytes. The positions of the latter are revealed by CC1 (marker of mature oligodendrocytes) and DAPI (nuclei) staining (right images).

Furthermore, mice treated intrathecally with the HDAC1/2 inhibitor Mocetinostat for 24 h showed robust increase of acetylated eEF1A in mature oligodendrocytes (CC1+), strongly suggesting that eEF1A1 is also deacetylated by HDAC1/2 in the CNS and that a similar mechanism controlling Sox10 expression and activity by acetylated eEF1A1 occurs in oligodendrocytes, such as in Schwann cells. In FIG. 11, the image on the bottom left shows higher levels of green fluorescence in the oligodendrocytes nuclei (can be derived from the positions of the red CC1 fluorescence, white arrows) than the image on the top left side.

Example 10

High levels of Acetylated eEF1A are Present inside Demyelinating Lesions of Human Brain from Patients with Multiple Sclerosis This example aims at assessing the relevance of the present findings in the context of demyelinating diseases in humans such as in multiple sclerosis. In this aim, the levels of acetylated eEF1A in oligodendrocytes present in the demyelinating lesions of brains from patients with multiple sclerosis were evaluated post-mortem.

Materials and Methods

Multiple sclerosis brain tissue samples were provided by the UK Multiple Sclerosis Tissue Bank (UK Multicentre Research Ethics Committee, MREC/02/2/39). Cryosections (10 μm) from fresh frozen tissue blocks were fixed overnight in 4% paraformaldehyde, washed with PBS and submitted to antigen retrieval in 10 mM citrate buffer, pH 6.0, at 65° C. for 2h. Sections were then blocked for 30 min at RT in blocking buffer (PBS pH 7.4, 0.3% Triton X-100, 10% normal donkey serum, 1% fish skin gelatin) and incubated with primary antibodies in blocking buffer overnight at 4° C. Sections were then incubated for 1 h in 10 mM $CuSO_4$, 50 mM $CH_3COONH_4$, pH 5.0, and next incubated with secondary antibodies in blocking buffer for 2 h at RT, counterstained with DAPI, washed and mounted using Fluorosave (Millipore). Antibodies: CC1 (mouse, 1:100, Calbiochem, cat. # OP80), Olig2 (goat, 1:100, R&D systems, cat. # AF2418), eEF1A-pan (Acetyl-Lys41) (rabbit, 1:500, Labforce, cat. # D12106). Secondary antibodies, donkey anti-mouse IgG-Cy3, donkey anti-rabbit IgG-Cy2 and donkey anti-goat IgG-Cy5, were purchased from Jackson ImmunoResearch.

Results

Figure 12:
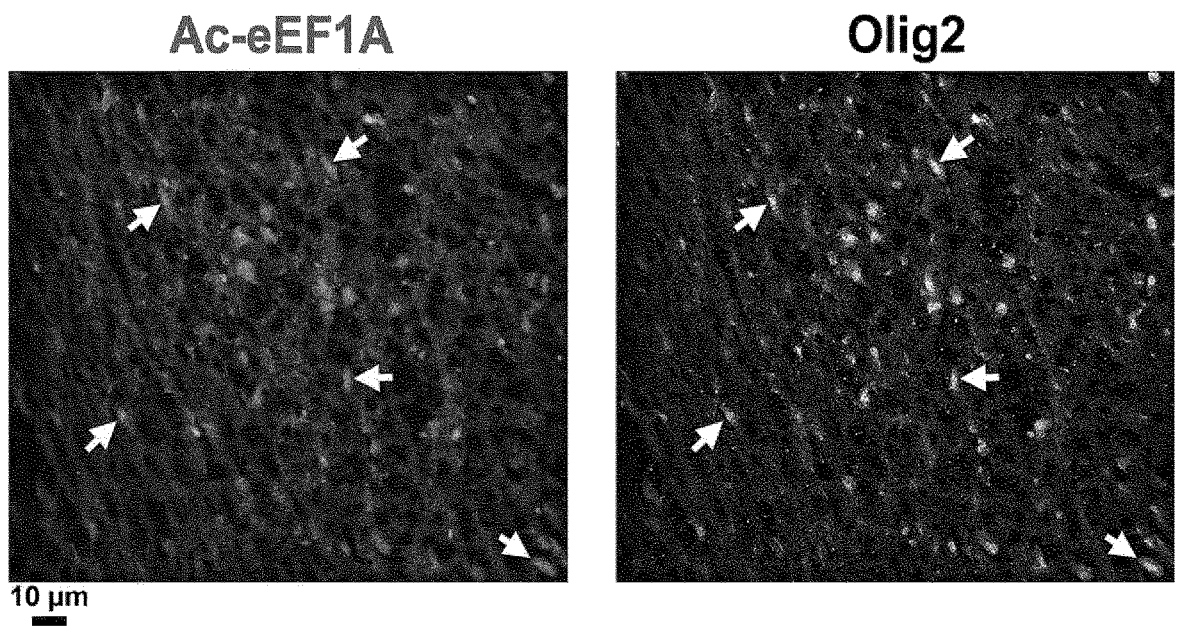
FIGS. 12A and 12B are immunofluorescence images obtained from tissue samples of brains from patients with multiple sclerosis. The samples shown in FIG. 12A are taken from inside multiple sclerosis lesions, whereas the samples in FIG. 12B were taken from normal appearing tissue.
Figure 12:
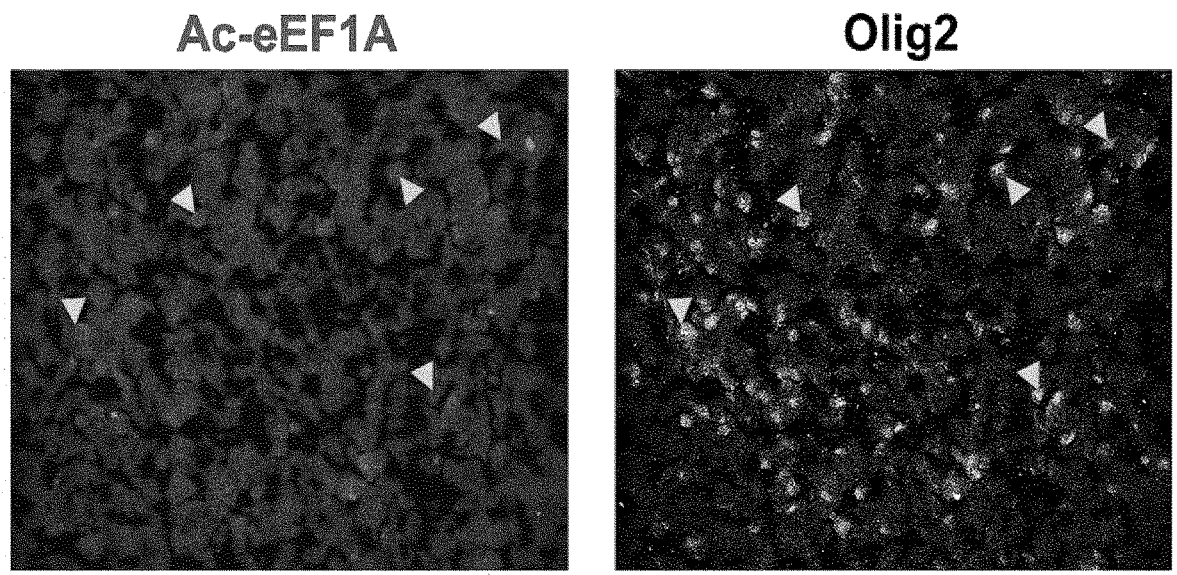

Immuno fluorescence analyses of acetylated eEF1A in oligodendrocytes of multiple sclerosis lesions were carried out. High levels of acetylated eEF1A were found in oligodendrocytes (cells positive for the oligodendrocyte marker Olig2) inside demyelinated lesions and at their border (FIG. 12A), but not in oligodendrocytes of the normal appearing tissue of the same human brain (FIG. 12B), suggesting that treatment with an HDAC2 activator such as theophylline may be useful to decrease acetylated eEF1A levels and thereby increase remyelination in patients with multiple sclerosis. In FIG. 12A, the left image shows higher green fluorescence in the oligodendrocyte nuclei (can be derived from the positions of the white Olig2 fluorescence on the right image, white arrows) than the image on the left side of FIG. 12B (blue arrowheads).

Contemplative Example 11

Treating of an MS Patient using a Combination Treatment

In this contemplative example, a group of female and male patients suffering from MS receiving theophylline [250 mg/day] during 1 month in addition to the standard treatment of interferon-β1a.

Surprisingly, in comparison to the average patients receiving only the standard treatment, the patients of this study showed in average a significantly faster remission following an attack (exacerbation) and in some cases complete stop of disease progression.

Thanks to the combination therapy according to the present invention, the MS patients experienced substantially increased life quality.

REFERENCES

1 Brügger, V. et al. Delaying histone deacetylase early response to injury accelerates conversion into repair Schwann cells and nerve regeneration. Nat. Comm. 8, 14272 (2017).

2 Jacob, C. et al. Schwann cell survival and myelination are critically dependent on HDAC1 and HDAC2 function. Nat. Neurosci. 14, 429-436 (2011).

3 Yamaguchi, T. et al. Histone deacetylases 1 and 2 act in concert to promote the Gl-to-S progression. Genes Dev. 24, 455-469 (2010).

4 Lindeboom, F. et al. A tissue-specific knockout reveals that Gata1 is not essential for Sertoli cell function in the mouse. Nucleic Acids Res. 31, 5405-5412 (2003).

5 Jacob, C., Grabner, H., Atanasoski, S. & Suter, U. Expression and localization of Ski determine cell type-specific TGFbeta signaling effects on the cell cycle. J. Cell Biol. 182, 519-530 (2008).

6 Monje, P. V., Soto, J., Bacallao, K. & Wood, P. M. Schwann cell dedifferentiation is independent of mitogenic signaling and uncoupled to proliferation: role of cAMP and JNK in the maintenance of the differentiated state. J. Biol. Chem. 285, 31024-31036 (2010).

7 Pereira, J. A. et al. Integrin-linked kinase is required for radial sorting of axons and Schwann cell remyelination in the peripheral nervous system. J. Cell Biol. 185, 147-161 (2009).

8 Fancy, S. P. et al. Axin2 as regulatory and therapeutic target in newborn brain injury and remyelination. Nat. Neurosci. 14, 1009-1016 (2011).

9 Zawadzka, M. et al. CNS-resident glial progenitor/stem cells produce Schwann cells as well as oligodendrocytes during repair of CNS demyelination. Cell Stem Cell. 6, 578-590 (2010)

The invention claimed is:

1. A method for increasing and/or promoting myelination after lesions to myelin of nerve cells or after a demyelinating event in said nerve cells, the method comprising administering, to an individual in need thereof, a pharmaceutical composition comprising a therapeutically effective amount of an activator of histone deacetylase (HDAC) 1 or 2 enzymatic activity and/or expression,
wherein said activator of HDAC is administered within 15 days after the occurrence of a demyelinating event in the CNS or after the diagnosis of a demyelinating event or condition,
wherein said activator of HDAC is theophylline or a pharmaceutically acceptable salt of theophylline, and wherein said theophylline or said pharmaceutically acceptable salt is administered at a daily dose of not more than 250 mg/day which dose is not pharmaceutically effective to inhibit phosphodiesterase.

2. The method of claim 1, which further promotes remyelination and/or prevents demyelination.

3. The method of claim 1, which further accelerates regeneration of nerve cells of the peripheral nervous system (PNS) and/or of the central nervous system (CNS).

4. The method of claim 1, wherein the individual has one or more diseases and/or conditions selected from the group consisting of: (1) traumatic injury of the PNS, (2) multiple sclerosis, (3) Charcot-Marie-Tooth disease, (4) Waardenburg syndrome, (5) Guillain-Barre syndrome, (6) chronic inflammatory demyelination polyneuropathy, (7) demyelination due to aging, diabetes or due to toxic agents, (8) demyelination and hypomyelination due to Acute disseminated encephalomyelitis, (9) demyelination and hypomyelination due to transverse myelitis, (10) demyelination and hypomyelination due to Leukodystrophy, (11) demyelination and hypomyelination due to Central pontine myelinolysis, (12) demyelination and hypomyelination due to Glioma, (13) schizophrenia, and (14) demyelination after traumatic lesion of the CNS.

5. The method of claim 4, wherein the disease and/or condition is multiple sclerosis.

6. The method of claim 1, wherein said activator of HDAC is an activator of HDAC2 deacetylase activity.

7. The method of claim 1, wherein said activator of HDAC increases HDAC1 and/or HDAC2 deacetylase activity in vivo.

8. The method of claim 1, wherein said activator of HDAC increases expressions of HDAC1 and/or HDAC2 in cells selected from Schwann cells, oligodendrocytes, and nerve cells.

9. The method of claim 1, for which further promotes and/or accelerates remyelination of nerve cells of the PNS after lesion, wherein said activator of HDAC is administered at the earliest 5 days after occurrence of the lesion.

10. The method of claim 1, which further increases and/or accelerates remyelination of nerve cells of the CNS after an attack to glia cells.

11. The method of claim 1, which further comprising administering an anti-inflammatory agent.

12. The method of claim 11, wherein said anti-inflammatory agent and said activator of HDAC are administered simultaneously and/or sequentially.

13. The method of claim 11, wherein said anti-inflammatory agent is selected from the group consisting of interferon β1a, glatiramer acetate, mitoxantrone, natalizumab, alemtuzumab, daclizumab, ocrelizumab, cladribine, fingolimod, dimethyl fumarate, ofatumumab, and corticosteroids.

14. The method of claim 1, wherein said pharmaceutical composition is administered at the earliest 5 days after occurrence of the demyelinating event in the CNS.

15. The method of claim 1, wherein said pharmaceutical composition further comprises a pharmaceutically acceptable carrier.

16. The method of claim 1, wherein said individual suffers from relapsing-remitting multiple sclerosis, and wherein said demyelinating event in the CNS is an attack on the myelin sheaths in the CNS of the individual.

17. The method of claim 1, wherein said method consists of administering theophylline or a pharmaceutically acceptable salt of theophylline.

* * * * *